United States Patent [19]
Rhee et al.

[11] Patent Number: 5,935,789
[45] Date of Patent: Aug. 10, 1999

[54] **AUTONOMOUSLY REPLICATING SEQUENCES, GAPDH GENE AND PROMOTER DERIVED FROM *HANSENULA POLYMORPHA*, EXPRESSION VECTORS CONTAINING SAME AND METHOD FOR THE SELECTION OF TRANSFORMANTS**

[75] Inventors: Sang-Ki Rhee, Seoul; Eui-Sung Choi, Daejeon; Chul-Ho Kim, Daejeon; Jung-Hoon Sohn, Daejeon; Hyun-Ah Kang, Daejeon; Hwa-Young Kim, Seoul, all of Rep. of Korea

[73] Assignee: Korea Institute of Science and Technology, Seoul, Rep. of Korea

[21] Appl. No.: 08/903,800

[22] Filed: Jul. 31, 1997

[30] Foreign Application Priority Data

Jan. 31, 1997 [KR] Rep. of Korea ................. 97-3173

[51] Int. Cl.$^6$ ............. C12Q 1/68; C12N 15/81; C12N 9/72; C12N 1/19
[52] U.S. Cl. .................. 435/6; 435/6; 435/29; 435/69.4; 435/69.5; 435/69.6; 435/69.51; 435/69.52; 435/320.1; 435/252.3; 435/254.1; 435/254.11; 435/255.6; 435/215; 435/206; 536/23.4; 536/23.7; 536/23.74; 536/24.1
[58] Field of Search ................ 435/6, 7.1, 7.31, 435/29, 69.1, 69.4, 69.5, 69.6, 69.51, 69.52, 320.1, 252.3, 254.1, 254.11, 255.6, 215, 206; 536/23.1, 23.2, 23.4, 23.7, 23.74, 24.1

[56] References Cited

PUBLICATIONS

Sohn, J.–H.; Choi, E.–S.; Kim, C.–H.; Agaphonov, M.O., Ter–Avanesyan, M.D.; Rhee, J.–S.; Rhee, S.–K.; A Novel Autonomously Replicating Sequence (ARS) for Multiple Integration in the Yeast *Hansenula polymorpha* DL–1, Journal of Bacteriology, vol. 178, No. 15, Aug. 1996, pp. 4420–4428.

*Primary Examiner*—David Guzo
*Attorney, Agent, or Firm*—Anderson, Kill & Olick, P.C.

[57] ABSTRACT

Autonomously replicating sequences(ARS), glyceraldehyde-3-phosphate dehydrogenase(GAPDH) gene and GAPDH promoter derived from *Hansenula polymorpha* DL-1(ATCC 26012); a vector for *H. polymorpha* which contains the novel ARS and is capable of inserting tandem repeating multiple copies of a polynucleotide encoding a foreign protein to the chromosome of *H. polymorpha*; a process for the production of a foreign protein in *H. polymorpha* by employing said vector; and a method for the selection of transformed *H. polymorpha* having multiple copies of integrated foreign genes.

29 Claims, 17 Drawing Sheets

EcoRV/StuI Digestion
MOX Probe

λ/HindIII UR2

BamHI Digestion
Sc-URA3 Probe

λ/HindIII UR2 pUREGF

AUTONOMOUSLY REPLICATING SEQUENCES, GAPDH GENE AND PROMOTER DERIVED FROM *HANSENULA POLYMORPHA*, EXPRESSION VECTORS CONTAINING SAME AND METHOD FOR THE SELECTION OF TRANSFORMANTS

FIELD OF THE INVENTION

The present invention relates to novel autonomously replicating sequences(ARS's), glyceraldehyde-3-phosphate dehydrogenase(GAPDH) gene and GAPDH promoter derived from *Hansenula polymorpha* DL-1(KTCT 0512 BP); a vector for *Hansenula polymorpha* which contains the ARS's and is capable of inserting multiple copies of a polynucleotide encoding a foreign protein into the chromosome of *Hansenula polymorpha* in multiple tandem repeats; a process for the production of said foreign protein in *Hansenula polymorpha* by employing said vector; and a method for the selection of transformed *Hansenula polymorpha* having the multiple copies of integrated foreign genes.

BACKGROUND OF THE INVENTION

*Saccharomyces cerevisiae* has been extensively studied as a host in biotechnological processes for the production of heterologous proteins of pharmaceutical interest. However, the productivity obtainable with this yeast species is low due to the lack of strong promoters and owing to the instability of transformed plasmid during a long-term culture under a nonselective condition. To deal with this instability problem, integrative transformation methods have been devised. For example, incorporation of multiple copies of genes encoding the heterologous proteins into specific sites in the chromosomal DNA was attempted by employing such targets as the transposable element Ty and ribosomal DNA plasmid. However, the copy number of the integrated genes resulting therefrom was observed to be low: that is, the aforementioned instability problem was left unresolved (Hinnen et al., "Gene Expression in Recombinant Yeast", in "Gene Expression in Microorganism", Smith, ed., Marcel Dekker, New York, 1995, p121).

A methylotrophic yeast, *Hansenula polymorpha*, on the other hand, possesses several strong promoters; and it is, therefore, an attractive cloning host for the production of heterologous proteins by way of multiple copy integration of heterologous genes into the chromosomal DNA thereof (Gleeson and Sudbery, *Yeast*, 4, 1(1988); Janowicz et al., *Yeast*, 7, 431(1991); Romanos et al., *Yeast*, 8, 423(1992); Faber et al., *Yeast*, 11, 1331(1995)). The strong promoters of *Hansenula polymorpha* include those associated with genes encoding methanol oxidase (MOX promoter), dihydroxyacetone synthase (DHAS promoter) and formate dehydrogenase (FMDH promoter). These promoters facilitate the expression of genes to the extent that the enzymes produced amount to 30 to 40% of the total cellular proteins (Gellissen et al., *Trends Biotechnol.*, 10, 413(1992)). Moreover, it is known to be relatively easy to integrate multiple copies of heterologous genes into the chromosomal DNA of *Hansenula polymorpha*, thereby enhancing the stability of the heterologous gene expression during long-term culturing (Hoolenberg and Janowicz, EP 299,108 A; Janowicz et al., *Nucleic Acid Res.*, 13, 3042(1985); Lederboer et al., *Nuclei Acid Res.*, 13, 3063(1985)). Due to the above-mentioned advantages, there have been many studies on the production of recombinant proteins using *Hansenula polymorpha* as a cloning host.

When a transforming plasmid containing a DNA sequence for self-copying activity(i.e., autonomously replicating sequence, ARS) is introduced to *Hansenula polymorpha*, it remains in the episomal state only transiently after the transformation, the transformants with the episomal plasmid showing a very low miotic stability. However, when the transformants are subjected to a stabilization procedure, e.g., a series of selections of a marker gene of the transforming plasmid by employing a selective medium and then culturing the resultant in a nonselective medium for several generations, the transformed cells become stabilized through an integration of the transforming plasmid into the chromosomal DNA (Roggenkamp et al., *Mol. Gen. Genet.*, 202, 302(1986)). During the process of such stabilization, certain cells acquire multiple copies of the heterologous gene in tandemly repeating gene units("multiple tandem repeats") integrated into the chromosomal DNA thereof.

The probability of obtaining cells having integrated multiple tandem genes increases with the self-copying ability of the ARS of the transforming plasmid (Roggenkamp et al., EP 0374282), but it is generally low. Thus, it is often required to go through time-consuming processes of selecting the cell having integrated multiple tandem genes; and, for this purpose, dominant selection markers have been used which confer varying degrees of resistance on the cell depending on the number of copies integrated therein.

Examples of the dominant selection markers mentioned above are: copper-resistant CUPI gene derived from *S. cerevisiae* (Fogel and Welch, *Proc. Natl. Acad. Sci., U.S.A.*, 79, 5342(1982)), methotrexate-resistant dihydrofolate reductase gene derived from mouse cDNA (Zhu et al., *Bio/Technol.*, 3, 451(1985)), G418-resistant aminoglycoside-3-phosphotransferase(APH) gene derived from Tn903 (Jamenez and Davies, *Nature*, 287, 869(1980)), hygromycin B-resistant hph gene derived from *Streptomyces hygcroscopicus* (Gritz and Davies, *Gene*, 25, 178(1983)), and sulfometuron methyl-resistant SMRI gene derived from *S. cerevisiae* (Casey et al., *J. Ind. Brew.*, 94, 93(1988)). Among the dominant selection markers mentioned above, the APH gene has been most frequently used in various yeast hosts. However, because promoters originating from *E. coli* are not adequately functional in yeasts, the selection efficiency of the *E. coli*-derived APH gene is only about 10% of that achievable with an auxotrophic marker (Jimenes and Davies, *Nature*, 287, 869(1983); Webster and Dickson, *Gene*, 26, 243(1983)). The use of PGK promoter derived from *S. cerevisiae* in place of the *E. coli*-derived promotor raised the APH expression efficiency to a level equivalent to that of an auxotrophic marker (Hadfield et al., *Curr. Genet.*, 18, 303(1990)). When the APH gene marker was attached to the MOX promoter and used in *Hansenula polymorpha*, the transformed cell was reported to have survived at a G418 concentration of 20 mg/ml(Gleeson and Sudbery, *Yeast*, 4, 1(1988)). It was also reported that the APH gene marker was tied to the promoter of alcohol dehydrogenase I(ADHI) of *S. cerevisiae* and used in a process to select cells containing multiple copies of heterologous genes (Janowicz et al., *Yeast*, 7, 431(1991)).

The MOX and FMDH promoters of *Hansenula polymorpha* are regulatory promoters whose expression is induced only when methanol is used as the carbon source (Gellisen et al., *Trends Biotechnol.*, 10, 413(1992)). Accordingly, when these promoters are employed in conjunction with foreign genes, it is possible to control the cell culturing step separately from the step of expressing recombinant proteins. Although this feature is useful when the expressed recombinant protein inhibits the cell growth, it is more convenient to employ a strong constitutive promoter which can be induced by any carbon source. One such promoter is the promoter of glyceraldehyde-3-phosphate dehydrogenase (GAPDH) gene, which has been widely used in the expression of heterologous proteins in *S. cerevisiae, Pichia pastoris* and other yeasts (Kniskern et al., *Gene*, 46, 135(1986);

Travis et al., *J. Biol. Chem.*, 260, 4384(1985); Hallewell et al., *Bio/Technol.*, 5, 363(1987); Rosenberg et al., *Methods in Enzymol.*, 185, 341(1990); Waterham et al., *Gene*, 186, 37(1997)).

As to autonomously replicating sequences(ARS's) of yeasts, it is known that the chromosomal DNA of *Saccharomyces cerevisiae* contains 300 to 400 ARS's, each being separated by 30 to 40 kb (Newlon, C. S., *Microbiol. Rev.*, 52, 568(1988)). Also, extensive studies have been conducted to characterize the ARS's of: *S. cerevisiae* (Foss et al., *Science*, 262, 2838(1993); Marahrens and Stillman, *Science*, 255, 817(1992); Rao et al., *Mol Cell Biol.*, 14, 7643(1994); Rowley et al., *Biochim. Biophys. Acta*, 1217, 239(1994); Theis and Newlon, *Mol Cell Biol.*, 14, 7652(1994)); Candida species (Cannon et al., *Mol. Gen. Genet.*, 221, 210(1990); Sasnaukas et al., *Yeast*, 8, 253(1992); *Yarrow lipolytica* (Fournier et al., *Proc. Natl. Acad. Sci.*, 90, 4912(1993); Matsuoka et al., *Mol. Gen. Genet.*, 237, 327(1993)); *Schizosaccharomyces pombe* (Caddle and Calos, *Mol. Gen. Genet.*, 14, 1796(1993); and Pichia species (Phillips Petroleum Co., U.S. Pat. No. 4,837,148).

There are two representative strains of *Hansenula polymorpha*: CBS4732(ATCC 34438, Hazeu et al., *Arch. Microbiol.*, 87, 185(1972)) and DL-1(ATCC 26012, Levine and Cooney, *Appl. Microbiol.*, 26, 982(1973)). The strain CBS4732 has been employed in the production of recombinant proteins; and several ARS's of *Hansenula polymorpha*(HARS's) of strain CBS4732 have been cloned (Roggenkamp et al., *Mol. Gen. Genet.*, 202, 302(1986); Bogdanova et al., *Yeast*, 11, 343(1995)). However, no studies have so far been conducted concerning the biochemical specificity of HARS's. The DL-1 strain, on the other hand, has never been utilized in a recombinant protein synthesis despite the advantages it offers over the CBS4732 strain: unlike CBS4732, it is thermotolerant at a growth temperature ranging from 37 to 50° C., capable of growing at a high methanol concentration due to its high methanol oxidase activity, and gives a higher protein yield in a comparative study wherein vectors containing the respective MOX promoters of the two strains are used (Sohn et al., *Appl. Microbiol. Biotechnol.*, 3, 65(1993). The MOX promoters of the two strains were found to have some differences at the sequence related to the methanol-induced expression (Godecke et al., *Gene*, 139, 35(1995)), and the homologous recombination efficiency was observed to be much higher with DL-1 than with CBS4732. Accordingly, the use of strain DL-1 as a cloning host in the production of recombinant proteins is expected to offer the following advantages over the case of using strain CBS4732.

First, because strain DL-1 grows fast in a medium having a high methanol concentration, precise control of the methanol concentration is not required for the induced expression of the heterologous gene. This characteristic property is particularly suitable when the production of the heterologous protein is growth-dependent. Second, as DL-1 grows well in a medium containing only methanol as the carbon source, it is presumed that the activity of DL-1 MOX promoter in the expression of the heterologous gene is higher than that of CBS4732. Third, DL-1 exhibits a high homologous recombination efficiency, which facilitates the integration of heterologous genes thereinto.

However, in order to employ *Hansenula polymorpha* DL-1 as the host in the production of recombinant proteins, it is necessary to find HARS's having high self-copying activities and also to establish an efficient method for selecting *H. polymorpha* cells carrying tandemly integrated foreign genes encoding said proteins.

SUMMARY OF THE INVENTION

Accordingly, it is an object of the present invention to provide a novel autonomously replicating sequence derived from *Hansenula polymorpha* DL-1(KCTC 0512BP).

Another object of the present invention is to provide glyceraldehyde-3-phosphate dehydrogenase(GAPDH) and GAPDH promoter genes derived from *Hansenula polymorpha*DL-1(KCTC 0512BP).

An additional object of the present invention is to provide a vector for *Hansenula polymorpha* which is capable of introducing a polynucleotide encoding a foreign protein into the chromosome of *Hansenula polymorpha* in a multiple tandem mode.

A further object of the present invention is to provide a process for the production of a foreign protein in *Hansenula polymorpha* by employing said vector.

A still further object of the present invention is to provide a simple process for the selection of *Hansenula polymorpha* which has polynucleotides encoding a foreign protein in multiple tandem repeats in its chromosome.

BRIEF DESCRIPTION OF THE DRAWINGS

The above and other objects and features of the present invention will become apparent from the following description of the invention taken in conjunction with the accompanying drawings, in which.

DETAILED DESCRIPTION OF THE INVENTION

Figure 1:
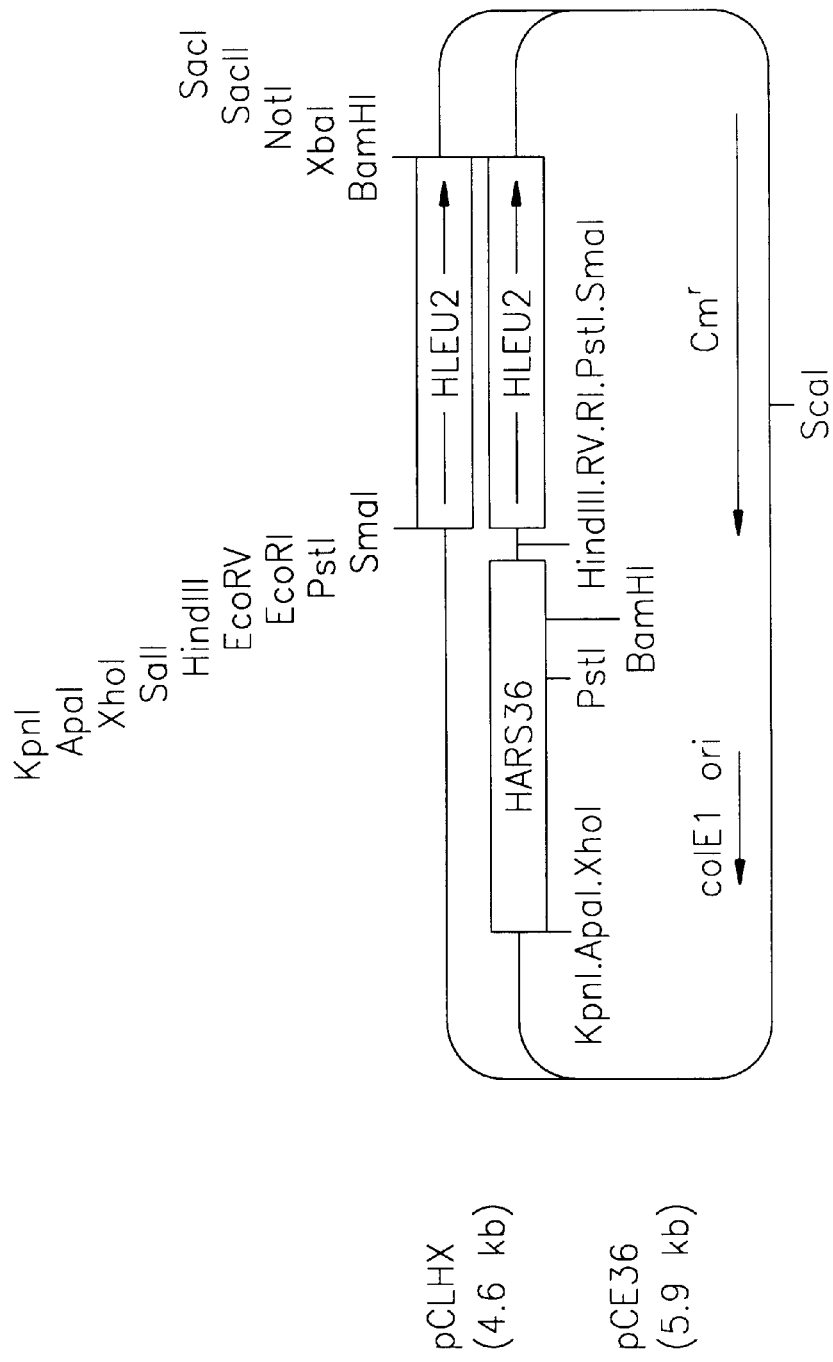
FIG. 1 shows a schematic illustration of the structures of plasmid pCLHX and pCE36.

All references and patent documents cited herein are hereby incorporated in their entirety by reference.

The present invention will now be more specifically illustrated hereinbelow.

1. Novel Autonomously Replicating Sequences

In accordance with one aspect of the present invention, there are provided autonomously replicating sequences ("ARS's") derived from *Hansenula polymorpha* DL-1 (KCTC 0512BP) which are capable of replicating a transforming DNA to multiple copies and integrating them into the chromosome of *Hansenula polymorpha* in tandem repeats. *Hansenula polymorpha* DL-1 was deposited on Aug. 14, 1998 with the Korea Research Institute of Bioscience and Biotechnology, Korean Collection for Type Cultures (Address: KCTC, KRIBB, #52, Oun-dong, Yusong-ku, Taejon, 305-333, Republic of Korea) under the terms of the Budapest Treaty on the International Recognition of the Deposit of Microorganism for the Purpose of Patent Procedure under the accession number of KCTC 0512BP.

The ARS's of the present invention have a repeating unit of 5'-GGGTGGCG-3' in their 3'-ends and the number of repetition of the unit is more than 15 times.

Exemplary ARS's of the present invention include HARS36 having the sequence of SEQ ID NO: 1, TEL188 having the sequence of SEQ ID NO: 2, TEL135 having the sequence of SEQ ID NO: 3 or TEL61 having the sequence of SEQ ID NO: 4:

```
HARS36(SEQ ID NO: 1, GenBank U31858)

GATCGAAGTA CCCTGGGGGT AGTATCTACT GCGCCACAAA GTCTGCCGTG   50
CGGATTCACC CAAGCAATTC GGAAGGAGCT GATCAGCACT AGGATCCGTG  100
TGATGGAGAT TGACCCTGGT GCTGTGGAGA CGGAGTTCTC GCTGGTGCGG  150
TTTGGCGGCG ATGCACAAAA GCCAGCAAGG TGTACGAAGG CTACGAGCCG  200
CTGAGTGCGA AGGACATTTC AGACGTGGTT GTGTTCAACT GCAGTCGGCG  250
GGCCAACGTG GTTGTGGCGG AGTCGGTGGT GTTTCCAACT GCGCAGGCGG  300
GAAGCTACCA TAGACATAGG AGTGAGCCAA GGGAGGGAAC AGAGAAGAAT  350
TAGAGAGGGA ATTAGAGAGG AATTAGAGCA AGTAGAGCTA TAGAAGAGAT  400
AAGCTAAGTC AAGAATTAGA GCAAGTAGGG GCAAGTTTAA TATATGTGGA  450
TTAATAAAGG TGAGAAATTA GATGGGAGGA GCGGCAGGAA ACGGTGTAGG  500
GATGCGGTGA GGGGAGCGGA CGCGGTTGGT TTTAGGATGC GGTCTGAGGG  550
TGGCGGGGTG GCGGGGTGGC GGGGTGGTGG GGTGGCGGGG TGGCGGGGTG  600
GCGGGGTGGC GGGGTGGCGG GGTGGCGGGG TGGCGGGGTG GCGGGGTGGC  650
GGGGTGGCGG GGTGGCGGGG TGGCGGGGTG GCGGGGTGGC GTGATCATCG  700
GGTACAACAT TGCCAACTTT GACTTCCCGT ACCTGATCAA CAGGGCTCGG  750
GCGCTCGGCG TCCACGACTT CCCGTACTTC TCGCGTCTGA AGAATAGCAA  800
GCAGGAGATC AAGGACACAT TTTTCAGCTC GCGCGCGTAC GGCAGCCGCG  850
AAAACAAGGT GGTCAATATT GAGGGCCGCA TGCAGCTGGA CCTGCTCCAA  900
TTCATCCAGC GCGAGTACAA ACTGCGCTCG TACACGCTGA ACGCGGTGTC  950
GGCACATTTT CTTAACGAAC AGAAAGAGGA TGTGCAGCAC TCGATCATCA 1000
CAGATCTCCA GAACGGCAAC CAGGAGACCA GAAGGCGGCT GGCAGTGTAC 1050
TGTCTGAAAG ACGCGTACTT GCCGTTGCGA CTAGCCGAAA AACTCATGTG 1100
TCTGGTCAAC TACACAGAGA TGGCCAGGGT GACCGGCGTG CCGTTCAGTT 1150
TCCTCCTCTC GCGTGGCCAG CAGATTAAGG TCATCTCGCA GCTGTTCCGC 1200
AAGTGTCTGG ACCTGGACAT TGTGATC                          1227

TEL188(SEQ ID NO: 2, GenBank U82170)

CTGCAGTCGG CGGGCCAACG TGGTTGTGGC GGAGTCGGTG GTGTTTCCAA   50
CTGCGCAGGC GGGAAGCTAC CATAGACATA GGAGTGAGCC AAGGGAGGGA  100
ACAGAGAAGA ATTAGCGAGG GAATTAGAGA GGAATTAGAG CAAGTAGAGC  150
TATAGAAGAG ATAAGCTAAG TCAAGAATTA GAGCAAGTAG GGGCAAGTTT  200
AATATATGTG GATTAATAAA GGTGAGAAAT TAGATGGGAG GAGCGGCAGG  250
AAACGGTGTA GGGATGCGGT GAGGGGAGCG GACGCGGTTG GTTTTAGGAT  300
GCGGTCTGAG GGTGGCGGGG TGGCGGGGTG GCGGGGTGGT GGGGTGGCGG  350
GGTGGCGGGG TGGCGGGGTG GCGGGGTGGC GGGGTGGCGG GGTGGCGGGG  400
TGGCGGGGTG GCGGGGTGGC GGGGTGGCGG GGTGGCGGGG TGGCGGGGTG  450
GCG                                                    453

TEL135(SEQ ID NO: 3, GenBank U82171)

CTGCAGTCGA CAGGCCAACG TGGTTGTGGC GGAGTCGGTG GTGTTTAGAG   50
AGGAATTAGA GCAAGTAGAA GTATAGAAGG AATAAGCCAA GTAGAGACAA  100
GTTTAATATA TGTAGATTAA TAAAGGTGAG GAATTAGATG GGGAGGAAGC  150
GGCAGGAAGC GGTGTAGGGA TGCGGCGAGG AAAGCAGAGG CAGCTGGTTT  200
CAGGACGCGG TCTGAGGCCT GGGGTGGCGG GGTGGCGGGG TGGCGGGGTG  250
GCGGGGTGGC GGGGTGGCGG GGTGGCGGGG TGGCGGGGTG GCGGGGTGGC  300
GGGGTGGCGG GGTGGCGGGG TGGCGGGGTG GCGGGGTGGC GGGGTGGCGG  350
GGTGGCGGGG TGGCGGGGTG GCGGGGTGGC GGGGTGGCGG GGTGGCGGGG  400
TGGCG                                                  405

TEL61(SEQ ID NO: 4, GenBank U82172)

CTGCAGTCGG CGGGCCAACG TGGTTGTGGC GGAGTCGGTG GTGTTTCCAA   50
GTGCGCAGGC GGGAAGCTAC CATAGACATA GGAGTGAGCC AAGGGAGGGA  100
ACAGAGAGGA ATTAGAGAGG GAATTAGAGA AGAATCAGAG CAAGTAGAGC  150
TATAGAAGGA ATAAGCCAAG TTAAGAATTA GAGCAAGTAG AGGCAAGTTT  200
AATATATGTA GATTAATAAA GGTGAGAAAT TAGATGGGGA GGAAGCGGCA  250
GGAAGCGGTG TAGGGATGCG GTGAGAAGAG CGGCCGAGCT GGTTTGAGGA  300
TGCGGTCTGA GGATTGGGGT GGCGGGGTGG CGGGGTGGCG GGGTGGCGGG  350
GTGGCGGGGT GGCGGGGTGG CGGGGTGGCG GGGTGGCGGG GTGGCGGGGT  400
GGCGGGGTGG CGGGGTGGCG GGGTGGCGGG GTGGCGGGGT GGCGGGGTGG  450
CGGGGTGGCG                                             460
```

HARS36 has three functional factors in the 407th–522nd ("Region A"), the 276th–406th ("Region B") and the 523rd–700th nucleotides ("Region C"), which affect the autonomous replicating activity thereof. When a *Hansenula polymorpha* strain is transformed with a plasmid containing HARS36 wherein Region A is removed, HARS36 losts the autonomous replicating activity completely. When the same strain is transformed with a plasmid containing HARS36 wherein Region B or C is removed, both the transformation efficiency and the growth rate of the transformant decreases, leading to an overall decrease of autonomous replicating activity of HARS36. Accordingly, it is concluded that Region A is indispensable for the autonomous replicating activity of HARS36, while Region B and C are necessary for the complete autonomous replicating activity of HARS36. Also, when a *Hansenula polymorpha* strain was transformed with a plasmid containing HARS36 wherein Region C is removed, the insertion of the plasmid into the chromosome of the host becomes sluggish. Accordingly, it is concluded that Region C is responsible for the plasmid insertion into the chromosome of a host cell.

On the other hand, an amino acid sequence deduced from the 700th–1227th nucleotides (Region D) of HARS36, which does not affect the autonomous replicating activity of HARS36, shows a homology of 84% with the 396th–597th amino acids of DNA polymerase III of *Saccharomyces cerevisiae* (Morrison et al., *Nucleic Acid Res.*, 20, 375 (1992)). It has been found that the three functional factors, i.e., Regions A, B and C, and Region D have been originated from different chromosomes.

TEL188 has regions having the same nucleotide sequence as the Regions A, B and C of HARS36, and TEL135 has a deletion in a part of Region B. The nucleotide sequences of TEL135 and TEL61 are analogous to that of TEL188 and the homologies among TEL188, TEL135 and TEL61 are more than 90%.

2. GAPDH gene and GAPDH promoter of *Hansenula polymorpha*

The present invention also provides a polynucleotide encoding GAPDH and GAPDH promoter derived from *Hansenula polymorpha* DL-1(ATCC 26012).

The polynucleotide encoding GAPDH of *Hansenula polymorpha* DL-1(ATCC 26012) has the nucleotide sequence of SEQ ID NO: 5.

```
SEQ ID NO: 5
CCTTTGCTCA ATGCCGTTTT GGTGATATCG ACCAATTGCT GGTTAACGGT   50
GTCGTTGCCG TACTTGTAAT AATAAGTACC GCAGCCAAAG GCTAATCTTG  100
GAATGCCCGA GGAGGTGGTT GGAATGCTCA TTTCGAATAC AGTCAACAAT  150
CAATTGAGTT TGTATTTATA GCCAATTGGT CATTAATAAT CAGGCTTCCT  200
GCATGGTTTA GAGGTTGGTC TAGACTACAT CCGTGCACCA GAAAAGAGGC  250
GGGCCACGGA GGAAAAGGTG ACAACTCGCA AAGTTGCAAC AACTGCTATG  300
GCTCCAGCAC GGTGCGTGGG GTAAAGACAA TCTCCGGGAA CCGGTCCCGA  350
AACCGAGAAA GAGGGTTTTA AGCCTGTGTC CTCTGCGGAG GTGGTGTAGC  400
ACTTCTTATT GTCCTTTGGG CCGCTCCGGC GGTAGAGCTT CCATGGAACA  450
ACCTTGCACG GACAGGCAAG TCCCCGAGAC GCCTTGTTGG GTGATGTCCA  500
CTTCTGGCTA TACAGAGCTT TATATCACCT TACTGAACGC TAGAGTAGAC  550
CCAATTCCCG GCTCACACCA CCCTTACATG CAGAGCTAAC CAATAAGGTA  600
ATTAATTAAC ACTATATAGC TCGTGGTGAA CACTGGCCCG GAGTAGTCAT  650
ACGTGTAGGT TTTTGGCGTG ATGAAAATCA GGTGGCGCAC GACTTTTCGT  700
AAAGTTCGGG AGGGAGTGCT GCAAACGGCA TATAAGGACC AGTTTTTCTC  750
GCACATTATC AATTGCTCTT TAGTACAAAG ATAATATAGA AACAATATGA  800
CCGCAAACGT TGGAATTAAT GGATTTGGAA GAATTGGTAG ACTGGTGTTG  850
AGAATTGCCT TGAGCAGAGA CGACATCAAC GTCATTGCTA TCAATGATCC  900
ATTCATTGCT CCTGATTACG CCGCTTACAT GTTCAAGTAC GACTCTACCC  950
ACGGAAAGTT CAAGGGAACT GTCACCCACG AGGGCAAGTA CTTGGTCATT 1000
AACGGCAAGA AGATTGAGGT CTTCCAAGAG AGAGACCCAG CAAACATCCC 1050
ATGGGGTAAG GAGGGCGTCG ACTACGTTCT TGACTCCACT GGAGTTTTCA 1100
CCACCATCGA GGGTGCTCAA AAGCACATTG ATGCTGGTGC CAAGAAGGTC 1150
ATCATCACTG CTCCATCTAA GGACGCTCCA ATGTTCGTCG TCGGTGTGAA 1200
CCACGAGGAG TACACTCCAG ACATCAAGAT CCTGTCTAAC GCTTCTTGTA 1250
CCACCATCTG TCTGGTTCCA CTGGCCAAGG TTATCACTGA CATCTTCGGA 1300
ATCGAGGAAG GTTTGATGAC CACCGTCCAC TCCATCACCG CTACTCAAAA 1350
GACTGTCGAC GGTCCATCCC ACAAGGACTG GAGAGGTGGT AGAACTGCTT 1400
CTGGTAACAT CATCCCATCC TCCACCGGTG CTGCCAAGGC TGTCGGAAAG 1450
GTCCTTCCAG CATTGGCCGG TAAGCTCACT GGTATGTCCA TGAGAGTCCC 1500
AACCACTGAT GTTTCTGTTG TTGACTTGAC CGTCAACCTT AAGAAGCCAA 1550
CCACCTACGA GGACATTTGT GCCACCATGA AGAAGGCTGC TGAGGGCCCA 1600
TTGGCTGGAA TTCTTGGATA CACCGACGAG GCTGTTGTTT CGTCTGACTT 1650
CTTGACCGAC AGCAGATCCT CTGTCTTTGA CGCCAAGGCC GGTATCTTGT 1700
TGACCCCAAC CTTCGTCAAG CTCGTTTCCT GGTACGACAA TGAGTACGGT 1750
TACTCTACCA GAGTTGTTGA CTTGCTTCAG CACGTTGCTA AGGTTTCCGC 1800
CTAAGCACGG CCTCATCTAC ATATTTACGG CTTAACTGAT TTTTATAGTT 1850
AAGGAGAAAA AAAGTTCAAC ATACGTCATT ATTATTGTAC GCGCTTTCGT 1900
GTTTCAAACT TGGCTGCCAT GATAAATAAA TCTATTGTTG CTTGCTATGT 1950
AAAAATTATT TGATTACTTC TTCCATGCAC TTTCTTTATT TGGATTGTGG 2000
TCCTGGTGGC ATTGGGGACT CTCTGGCATT ATACCCGTAT CCTGATACGG 2050
AACCGTTCTA AATATATTTC GCGACAATTC AGGAGCCGCA CGCTGCTTCT 2100
AGCGCATCAT GAGATCCACG TCATGCATGG TTGTAGACAA GGACAAGGGG 2150
CAGTAGCTCA GAAGGGCGTC GTGTTCTGGA CCGCATATGG ATACAATCAA 2200
TATCGGCATT GTTTTCGGTA CTGGGCACCT GCTTGCTGCT CAATCACCTC 2250
TTGTCGCTCC CCGCTCCAAT CTGATTTTCG CGTGAATAGG GCAAAAAAAA 2300
ATTCTCTGCC GGCTTGGGGC TGATCGGTGC ATTGAAATTT CCTTATACGT 2350
GTTCCAGGTT TCAATTTACT CTAGA                            2375
```

The polynucleotide coding for GAPDH of *Hansenula polymorpha* having the sequence of SEQ ID NO: 5 can be synthesized by a conventional DNA synthesizer, or can be obtained from the genomic DNA of *Hansenula polymorpha* by a Southern blotting analysis employing GAPDH gene of *Saccharomyces cerevisiae* as a probe.

The amino acid sequence deduced from the nucleotide sequence of SEQ ID NO: 5 has a homology of 72% with the GAPDH of *Saccharomyces cerevisiae* and has the sequence of SEQ ID NO: 6.

3. Expression Vectors and Transformants

In accordance with another aspect of the present invention, there is provided a vector system for *Hansenula polymorpha* which comprises the novel ARS of the present invention, i.e., HARS36, TEL188, TEL135 or TEL61. The ARS plays a critical role in the introduction of the vector containing a polynucleotide encoding a foreign protein into

```
SEQ ID NO: 6
Met Thr Ala Asn Val Gly Ile Asn Gly Phe Gly Arg Ile Gly Arg   15
Leu Val Leu Arg Ile Ala Leu Ser Arg Asp Asp Ile Asn Val Ile   30
Ala Ile Asn Asp Pro Phe Ile Ala Pro Asp Tyr Ala Ala Tyr Met   45
Phe Lys Tyr Asp Ser Thr His Gly Lys Phe Lys Gly Thr Val Thr   60
His Glu Gly Lys Tyr Leu Val Ile Asn Gly Lys Lys Ile Glu Val   75
Phe Gln Glu Arg Asp Pro Ala Asn Ile Pro Trp Gly Lys Glu Gly   90
Val Asp Tyr Val Leu Asp Ser Thr Gly Val Phe Thr Thr Ile Glu  105
Gly Ala Gln Lys His Ile Asp Ala Gly Ala Lys Lys Val Ile Ile  120
Thr Ala Pro Ser Lys Asp Ala Pro Met Phe Val Val Gly Val Asn  135
His Glu Glu Tyr Thr Pro Asp Ile Lys Ile Leu Ser Asn Ala Ser  150
Cys Thr Thr Asn Cys Leu Ala Pro Leu Ala Lys Val Ile Asn Asp  165
Ile Phe Gly Ile Glu Glu Gly Leu Met Thr Thr Val His Ser Ile  180
Thr Ala Thr Gln Lys Thr Val Asp Gly Pro Ser His Lys Asp Trp  195
Arg Gly Gly Arg Thr Ala Ser Gly Asn Ile Ile Pro Ser Ser Thr  210
Gly Ala Ala Lys Ala Val Gly Lys Val Leu Pro Ala Leu Ala Gly  225
Lys Leu Thr Gly Met Ser Met Arg Val Pro Thr Thr Asp Val Ser  240
Val Val Asp Leu Thr Val Asn Leu Lys Lys Pro Thr Thr Tyr Glu  255
Asp Ile Cys Ala Thr Met Lys Lys Ala Ala Glu Gly Pro Leu Ala  270
Gly Ile Leu Gly Tyr Thr Asp Glu Ala Val Val Ser Ser Asp Phe  285
Leu Thr Asp Ser Arg Ser Ser Val Phe Asp Ala Lys Ala Gly Ile  300
Leu Leu Thr Pro Thr Phe Val Lys Leu Val Ser Tyr Asp Asn      315
Glu Tyr Gly Tyr Ser Thr Arg Val Val Asp Leu Leu Gln His Val  330
Ala Lys Val Ser Ala                                          335
```

The GAPDH promoter derived from *Hansenula polymorpha* DL-1(KCTC 0512BP) has the nucleotide sequence of SEQ ID NO: 7.

the chromosome of a host in a multiple tandem mode, providing a high transformation efficiency. The position of

```
SEQ ID NO: 7
CCTTTGCTCA ATGCCGTTTT GGTGATATCG ACCAATTGCT GGTTAACGGT  50
GTCGTTGCCG TACTTGTAAT AATAAGTACC GCAGCCAAAG GCTAATCTTG 100
GAATGCCCGA GGAGGTGGTT GGAATGCTCA TTTCGAATAC AGTCAACAAT 150
CAATTGAGTT TGTATTTATA GCCAATTGGT CATTAATAAT CAGGCTTCCT 200
GCATGGTTTA GAGGTTGGTC TAGACTACAT CCGTGCACCA GAAAAGAGGC 250
GGGCCACGGA GGAAAAGGTG ACAACTCGCA AAGTTGCAAC AACTGCTATG 300
GCTCCAGCAC GGTGCGTGGG GTAAAGACAA TCTCCGGGAA CCGGTCCCGA 350
AACCGAGAAA GAGGGTTTTA AGCCTGTGTC CTCTGCCGAG GTGGTGTAGC 400
ACTTCTTATT GTCCTTTGGG CCGCTCCGGC GGTAGAGCTT CCATGGAACA 450
ACCTTGCACG GACAGGCAAG TCCCCGAGAC GCCTTGTTGG GTGATGTCCA 500
CTTCTGGCTA TACAGAGCTT TATATCACCT TACTGAACGC TAGAGTAGAC 550
CCAATTCCCG GCTCACACCA CCCTTACATG CAGAGCTAAC CAATAAGGTA 600
ATTAATTAAC ACTATATAGC TCGTGGTGAA CACTGGCCCG GAGTAGTCAT 650
ACGTGTAGGT TTTTGGCGTG ATGAAAATCA GGTGGCGCAC GACTTTTCGT 700
AAAGTTCGGG AGGGAGTGCT GCAAACGGCA TATAAGGACC AGTTTTTCTC 750
GCACATTATC AATTGCTCTT TAGTACAAAG ATAATATAGA AACAAT      796
```

The GAPDH promoter of the present invention is advantageous in that it is a strong constitutive promoter which does not require a separate expression induced by a particular carbon source.

Moreover, the present invention also includes polynucleotides which are substantially identical to SEQ ID NO's 1, 2, 3, 4, 5 and 7, and which are functionally equivalent with these sequences. The term "substantial identity" means that two polynucleotides, when optimally aligned, such as by computerized implementations of known algorithms (e.g., GAP, BESTFIT, FASTA and TFASTA in the Wisconsin Genetics Software Package, Genetics Computer Group (GCG), 575 Science Dr., Madison, Wis., or BlastN and BlastX available from the National Center for Biotechnology Information using default parameters), or by inspection, share at least 70% sequence identity, preferably at least 80%, more preferably at least 90% and, most preferably, at least 95%.

ARS relative to the polynucleotide encoding the desired foreign protein is not critical.

Depending on the nature of the desired protein, the promoter, the transcription terminator and the replication system employed, there may exist various combinations of expression vectors.

The desired proteins which may be produced by using the expression vectors are of any useful kind, e.g., hirudin, human epidermal growth factor(hEGF), human serum albumin(HSA), prourokinase, urokinase, human $\alpha_1$-antitrypsin, hepatitis B surface antigen(HBsAg), lipocortins, interferons, lysozyme, interleukins, colony stimulating factors, tissue plasminogen activators, insulin, factor VIII, superoxide dismutase, calcitonin, insulin-like growth factors, growth hormones, etc.

The vector of the present invention may comprise the novel GAPDH promoter of *Hansenula polymorpha* DL-1 (KCTC 0512BP) as a promoter for the constitutive production of a foreign protein. The GAPDH promoter may be the full-length polynucleotide of SEQ ID NO: 7 or a fragment thereof, e.g., those having 219th–96th(GAP578), 441st–796th (GAP356), 505th–796th (GAP292), 546th–796th(GAP251), 651st–796th(GAP146) or 736th–796th(GAP61) nucleotides of SEQ ID NO: 7. When the GAPDH promoter of Hansenula polymorpha DL-1 (KCTC 0512BP) is used in the present vector, a polynucleotide encoding the desired protein may be inserted alone into the vector after the 3'- end of the promoter, or it may be inserted into the vector in the form of a fused polynucleotide wherein the polynucleotide encoding the desired protein is fused with the GAPDH gene or a fragment thereof derived from Hansenula polymorpha DL-1(KCTC 0512BP).

The present invention also provides an expression and selection vector, which comprises a selection cassette containing an ARS derived from Hansenula polymorpha DL-1 (KCTC 0512BP), a promoter, a dominant selection marker located in the downstream of said promoter, and an auxotrophic marker; and an expression cassette containing a promoter, a polynucleotide encoding a foreign protein, which is located in the downstream of said promoter; and a terminator which is located in the downstream of said polynucleotide.

In this vector, the ARS, which has a repeating unit of 5'-GGGTGGCG-3' in its 3'-end, may be HARS36, TEL188, TEL135 or TEL61, and the GAPDH promoter may be the full-length polynucleotide of SEQ ID NO: 7 or a fragment thereof, e.g., GAP578, GAP356, GAP292, GAP251, GAP146 or GAP61. The auxotrophic marker may be a gene responsible for nutrient synthesis, e.g., leucine synthesis gene( LEU2) and uracil synthesis gene(URA3) of a yeast (e.g., Hansenula polymorpha and Saccharomvces cerevisiae), preferably, LEU2. The dominant selection marker may be a gene providing antibiotic-resistance, e.g., aminoglycoside-3-phosphate transferase(APH) gene derived from E. coli transposon Tn903 or Tn5.

Most preferable vector of the present invention comprises a selection cassette consisting of the novel ARS of the present invention, a fusion gene of GAPDH promoter derived from Hansenula polymorpha DL-1(KCTC 0512BP) and APH gene, and LEU2 gene. In accordance with the size of GAPDH promoter, the copy number of the transformed gene may vary and it increases up to 50 copies when GAP61 is used. Moreover, it is possible to regulate the copy number of the transformed gene in the range from one to several hundreds by adjusting the concentration of antibiotic G418 in a medium to the range from 0.5 to 20 mg/ml. This vector is advantageous in that many foreign gene copies can be introduced into the chromosome of a host cell due to a high transformation efficiency of the strong ARS of the present invention and that the transformants can be selected easily due to the presence of dose-dependent dominant selection marker.

The vector of the present invention can be used for the expression of a foreign gene or selection of the transformant. It can be used in ligation with other known vectors, e.g., bacteria, yeasts, fungi and animal cells.

A Hansenula polymorpha cell may be transformed by the expression vector of the present invention in accordance with a conventional method, e.g., the lithium chloride-DMSO method (Hill et al., Nucleic Acid Res., 19, 5791 (1991)). Transformed Hansenula polymorpha cells are cultured on a suitable medium under a condition selected considering the host strain and the vector employed, and the desired protein may be obtained by collecting the yeast cell and purifying the desired protein therefrom or by purifying the secreted protein from the culture medium in case when a secretion signal sequence is used in the vector.

4. Method for the selection of transformants

The present invention provides a method for the selection of Hansenula polymorpha transformant having multiple copies of integrated foreign genes, which comprises the steps of:

(a) transforming Hansenula polymorpha with the expression and the selection of the present invention;

(b) culturing the transformed Hansenula polymorpha on a minimal medium to select transformants;

(c) culturing and subculturing the selected transformants on a composite medium to stabilize the vector in the transformants; and (d) culturing the stabilized transformants on a selective medium containing an antibiotic to select transformants resistant to the antibiotic.

In step (b), the minimal medium may be one of the conventional minimal media, and, it contains preferably 0.67% yeast nitrogen base without amino acid, 2% glucose and 2% bacto agar.

For the stabilization of the vector in step (c), the transformants may be subjected to subcultures until 10 to 100 generations, preferably, until 50 generations. The composite medium may contain 1 to 50 g, preferably, 10 g of yeast extract, 1 to 60 g, preferably, 20 g of Bacto-peptone and 1 to 50 g, preferably, 20 g of glucose or glycerol per 1 l of distilled water.

In step (d), the selective medium may contain an antibiotic plus a minimal or a composite medium. Exemplary selective medium may contain 0.3 to 4.0 mg/ml, preferably, 4.0 mg/ml of an antibiotic. The selection of the antibiotic depends on the dominant selection marker used in the vector, and, for instance, if APH gene is used as the dominant selection marker, a selection medium containing G418 is used. Further, as the concentration of the antibiotic increases, the copy number of plasmid contained in the selected transformant increases, while the number of transformants which have survived in the selective medium decreases.

The selection method of the present invention is advantageous in that it is possible to select the Hansenula polymorpha transformant having multiple copies of integrated foreign gene in a short time with little effort.

The following Examples are intended to further illustrate the present invention without limiting its scope; and the experimental methods used in the Examples can be practiced in accordance with the Reference Example given herein below, unless otherwise stated.

Further, percentages given below for solids in solid mixtures, liquids in liquids and solids in liquids are on a wt/wt, vol/vol and wt/vol basis, respectively, unless specifically indicated otherwise.

REFERENCE EXAMPLE (1) Transformation of microorganisms

Transformation of a H. polymorpha cell was carried out in accordance with the lithium chloride-DMSO method (Hill et al., Nucleic Acid Res., 19, 5791(1991)). Transformation of an E. coli cell was carried out in accordance with the SEM method (Inuoue et al., Gene, 96, 23(1990)).

(2) Southern blotting analysis

The Southern blotting analysis was performed in accordance with Southern method (Southern, E. M., J. Mol. Biol., 98, 503(1975)) by employing a hybridization solution (5× SSC, 0.1% N-lauroyl sarcosine, 0.02% SDS, 5% blocking reagent, 50% formamide) in 42° C. hybridization oven (Hybaid, U.K.). A probe was prepared by employing Non-radioactive DNA Labeling and Detection Kit (Boehringer Mannheim, Germany).

(3) Determination of copy number of introduced gene

The copy number of introduced gene was determined from a Southern densitogram by employing an image analysis system (Bio-Rad, Model GS-700).

(4) Determination of nucleotide sequence

The nucleotide sequence of a gene was determined by employing ABI Prism Dye Terminator Cycle Sequencing Ready Reaction Kit (Perkin-Elmer Cetus, U.S.A.) and DNA sequencer (Model 373A, Applied Biosystems, U.S.A.).

EXAMPLE 1

Preparation of HARS36

The autonomously replicating sequences (ARS's) of *H. polymorpha* were screened for those having activities for multiple-tandem integration as follows:

(Step 1) Preparation of recombinant plasmid pCLHX

Plasmid p18B1 (Agaphonov et al., *Yeast*, 10, 509(1994)) containing leucine 2(LEU2) gene of *H. polymorpha* was treated with restriction enzyme XhoII to obtain a 1.2 kb DNA fragment, which was inserted into plasmid pBC KS+ (Stratagen Co.) to obtain plasmid pCLHX carrying the LEU2 gene of *H. polymorpha* (FIG. 1).

(Step 2) Preparation of genomic library of *H. Polymorpha*

The genomic DNA of *H. polymorpha* DL-1(KCTC 0512BP) was isolated in accordance with Cryer's method (Campbell & Duffus, *Yeast*, p107, IRL Press (1988)) and cut with restriction enzyme Sau3A1. Two nucleotides, G and A, were added to each end of the resultant DNA fragments using Klenow DNA polymerase and the resultant DNA fragments were separated by electrophoresis to isolate DNA fragments of 500 to 1,5000 bp.

Plasmid PCLHX obtained in (Step 1) was cleaved with restriction enzyme SalI and two nucleotides were added to each end of the resulting fragment using Klenow DNA polymerase, and ligated with the DNA fragments prepared above to obtain a genomic plasmid library of *H. polymorpha*

*E. coli* DH5α was transformed with the genomic plasmid library according to SEM method (Inoue et al., *Gene*, 96, 23(1990)), and the transformed *E. coli* was spread on a LB medium (trypton 10 g, sodium chloride 10 g and bactoagar 20 g per l) containing 30 μg/ml of chloramphenicol and incubated at 37° C. overnight to obtain 5×10$^4$ colonies. DNA was extracted from the colonies to obtain an amplified library.

(Step 3) Transformation of *H. polymorpha* and stabilization of transforming plasmid

*H. polymorpha* DL-1(leu2) (NPO Biotechnologia, Moscow, Russia), which is a leu⁻ strain of *H. polymorpha* DL-1(KCTC 0512BP), was transformed with the genomic library in accordance with the lithium acetate method (Bogdanova et al., *Yeast*, 11, 343(1995)). The transformant was spread on a minimal medium (0.67% yeast nitrogen base without an amino acid, 2% glucose and 2% bactoagar) and incubated at 37° C. for three days to obtain transformants.

The transformants were subjected to a stabilization procedure, i.e., the transformants were cultured and subcultured on a composite medium (1% yeast extract, 2% Bactopeptone, 2% glucose and 2% bactoagar) for 48 hours, and then on a minimal medium for 24 hours according to the replica method to induce integration of the plasmid into the chromosome.

To examine whether or not the plasmid was indeed integrated in the chromosome, *H. polymorpha* transformants subjected to the stabilization procedure were subcultured on a composite medium until about twenty generations. The cultured transformants were plated on a composite medium and also on a minimal medium, and cultured at 37° C. for 3 days. Numbers of colonies formed on the two media were counted and compared. The result shows that leucine selective marker preservation was almost 100%.

To further confirm the plasmid integration into the chromosome, total DNA was extracted from *H. polymorpha* transformants subjected to the stabilization, and *E. coli* DH5α was transformed with total DNA. *E. coli* transformant was selected on LB medium containing 30 μg/ml of chloramphenicol, but no colony was formed.

DNA extracted from *H. polymorpha* having plasmid integrated into the chromosome thereof would not transform *E. coli*, the above result confirm the fact that the plasmid had been integrated in the chromosome of *H. polymorpha*.

(Step 4) Selection of multiple-tandem integrating ARS

DNA was isolated from the stabilized transformant obtained in (Step 3) by Cryer's method (Campbell & Duffus, supra), cut with restriction enzyme ScaI and, then, self-ligated to form a plasmid. *E. coli* DH5α was transformed with said plasmid, and transformant was cultured on LB medium containing 30 μg/ml of chloramphenicol.

As plasmid pCLHX has a ScaI restriction site in the chloramphenicol resistant(Cm$^R$) gene, *E. coli* transformed by integrating a single copy of ARS into the chromosome thereof would not be resistant to chloramphenicol, but *E. coli* transformed by incorporating multiple copies of ARS in multiple-tandem repeats would be chloramphenicol-resistant.

In line with this expectation, seven *E. coli* transformant colonies showing chloramphenicol resistance were selected. Those selected transformants contained seven new plasmids having DNA fragments which were different with pCLHX. These plasmids contained DNA fragments of 700 to 1,500 bp, and they were designated pCE11, pCE24, pCE35, pCE36, pCE37, pCE48 and pCE410, respectively.

Restriction analyses showed that pCE24, pCE35 and pCE36 contained an identical DNA fragment which is different from those obtained from pCE11, pCE37, pCE48 and pCE410. That is, five different DNA fragments were isolated which are multiple-tandem integrating ARS's of *H. polymorpha*.

(Step 5) Autonomously replicating (AR) activity of multiple-tandem integrating ARS of *H. polymorpha*

To confirm the AR activity of five DNA fragments obtained in Step 4, transformation and Southern blotting were conducted.

1) Transformation efficiency

*H. polymorpha* DL-1L(leu2) was transformed with each of the seven plasmids obtained in the Step 4 in accordance with the lithium acetate method and the number of transformants per μg of the plasmid was measured, wherein the plasmid concentration was determined by measuring an optical density at 260 nm with a UV spectrophotometer. Plasmid PCLHX prepared in Step 1, which contains no ARS, was used as a control. Also examined as comparative groups were plasmid YEp13 (Berardi and Thomas, *Curr. Genet.*, 18, 169(1990)) which contained LEU2 gene of the *Saccharomyces cerevisiae* and had an AR activity in *H. polymorpha* as well as pA2 and pA3 (Bogdanova et al., *Yeast*, 11, 343(1998)) which contained HARS2 and HARS3 of CBS 4732, respectively. The result is shown in Table 1.

TABLE 1

| Plasmid | Number of Transformants/ µg plasmid |
|---|---|
| pCLHX | 5 |
| YEp13 | 50 |
| pA2 | 400 |
| pA3 | 600 |
| pCE11 | 1000 |
| pCE24 | 2850 |
| pCE35 | 2600 |
| pCE36 | 2950 |
| pCE37 | 650 |
| pCE48 | 900 |
| pCE410 | 1100 |

As shown in Table 1, all plasmids containing ARS had remarkably higher transformation efficiencies as compared with the control plasmid PCLHX containing no ARS. Plasmids of the present invention had higher transformation efficiencies than the comparative plasmids containing ARS derived from strain CBS 4732, and in particular plasmids pCE24, pCE35 and pCE36 had significantly higher transformation efficiencies than others.

E. coli DH5α carrying plasmid pCE36 (E. coli DH5α/ pCE36) was deposited on Jul. 24, 1997 with the Korean Collection for Type Cultures (KCTC) (Address: KCTC, KRIBB, #52, Oun-dong, Yusong-ku, Taejon, 305-333, Republic of Korea) under the terms of the Budapest Treaty on the International Recognition of the Deposit of Microorganism for the Purpose of Patent Procedure under the accession number of KCTC 0352BP.

2) Southern blotting analysis

To examine the position of a transforming plasmid DNA in the transformant before and after the stabilization procedure, a Southern blotting analysis was carried out as follows:

The DNAs of the transformants after transformation and those after stabilization procedure of Step 4 were isolated, electrophoresed on a 1% agarose gel, and transferred on a nitrocellulose membrane. The membrane was blotted with a plasmid pBC KS+ (Stratagen Co.) labeled with digoxigenin (DIG) as a probe.

Figure 2A:
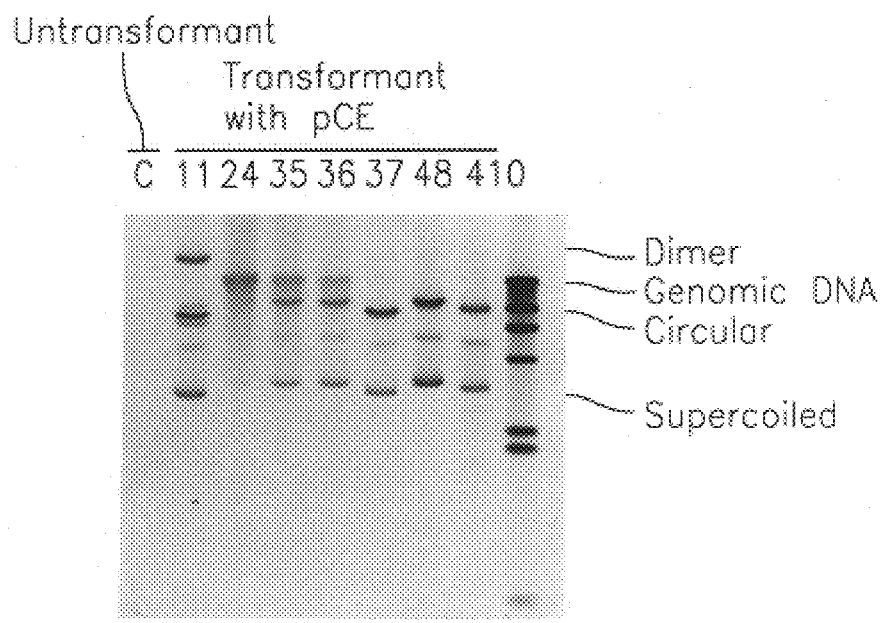
FIGS. 2A and 2B represent the results of Southern blotting analyses confirming the position of a transforming plasmid, pCE36 containing HARS36 before and after the stabilization process, respectively.
Figure 2B:
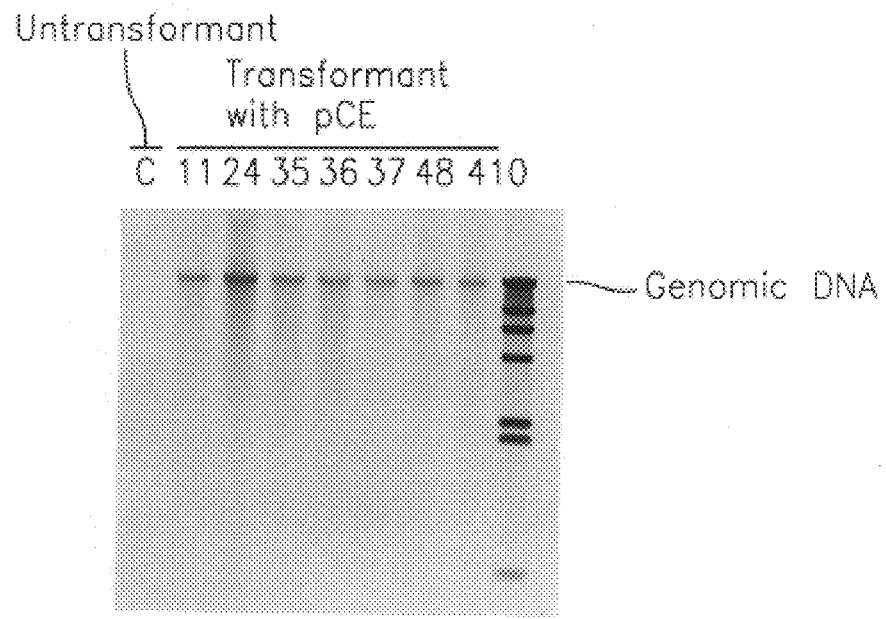

The results are shown in FIGS. 2A and 2B.

As FIG. 2a shows, both circular and supercoiled forms of plasmids were observed after the transformation, whereas no plasmid was detected in the non-transformed cells. This result thus suggest that all plasmids containing ARS can replicate autonomously in H. polymorpha.

The result in FIG. 2b shows, on the other hand, that the transforming plasmid was integrated into the chromosome after the stabilization procedure, i.e., the transforming plasmid exists not in the form of a plasmid but in a form integrated with the chromosome.

In cases of plasmids pCE24, pCE35 and pCE36, integrated forms thereof were detected even before the stabilization procedure. This suggests that the ARS's of said plasmids are much more easily integrated into the chromosome than ARS's of other plasmids. The 1.2 kb ARS of plasmid pCE36, in particular, which was designated as HARS36, was recognized for its high transformation efficiency and easy integrating into the chromosome.

EXAMPLE 2
Characteristics of HARS36
(1) Integration of a gene

To examine the integration pattern of plasmid pCE36 containing the HARS36, H. polymorpha DL-1L was transformed with plasmid pCE36, and the resulting transformants were cultured on a minimal medium. From the colonies formed, ten transformants were randomly selected and subjected to the stabilization procedure of Step 3 of Example 1 to integrate the plasmid into the chromosome. The stabilized transformants were cultured on a selective medium (0.67% yeast nitrogen base without amino acid, 2% glucose), and entire total DNAs of transformants were isolated, cut with restriction enzyme ScaI, and subjected to Southern blotting analysis as in Step 5 of Example 1 using plasmid pBC KS+ labeled with a DIG as a probe.

Figure 3A:
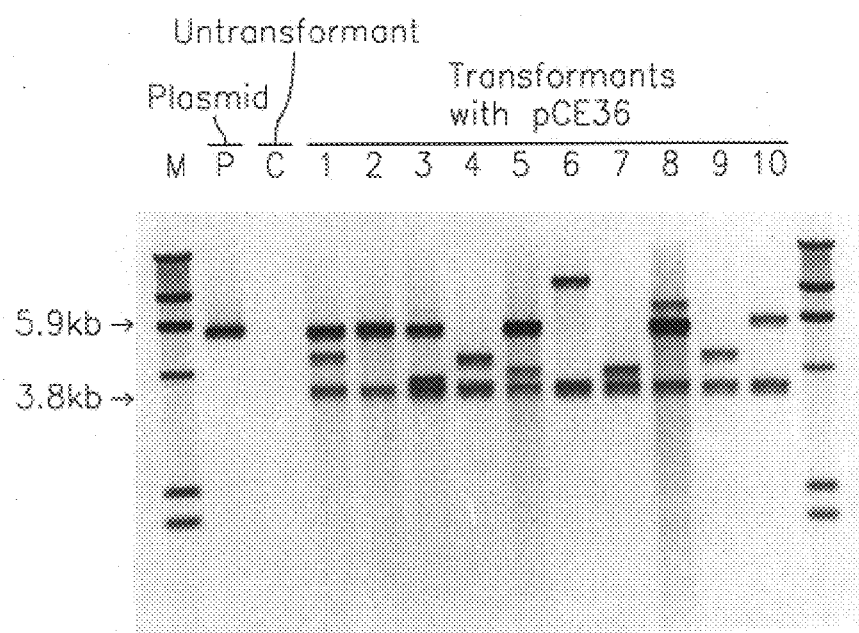
FIGS. 3A and 3B disclose the results of Southern blotting analyses confirming the form and position of a transforming plasmid, pCE36 containing HARS36 inserted in the chromosome, respectively.

In this analysis, DNAs having integrated plasmids would give a strong band of 5.9 kb fragment of plasmid pCE36 and two weak bands of terminal fragments. The results are illustrated in FIG. 3a wherein the M line presents size markers representing 23.0, 9.4, 6.6, 4.4, 2.3, 2.2 and 0.56 kb from the top. The results in FIG. 3a shows that for six out of ten transformants examined, strong bands at 5.9 kb each accompanied by two weak bands were observed. This suggests that pCE36 was integrated into the chromosome of six transformants in a multiple-tandem manner.

A 3.8 kb band was also observed for each of the ten transformants, which suggests that plasmid pCE36 was integrated in a similar position of the chromosome in all cases examined.

To determine the position of the chromosome where plasmid pCE36 was integrated, DNA of the transformant of line 8 was digested with exonuclease Bal31 for a measured length of time, and then cut with restriction enzyme ScaI. DNA fragments thus obtained were blotted using the probe mentioned above as in Step 5 of Example 1.

Figure 3B:
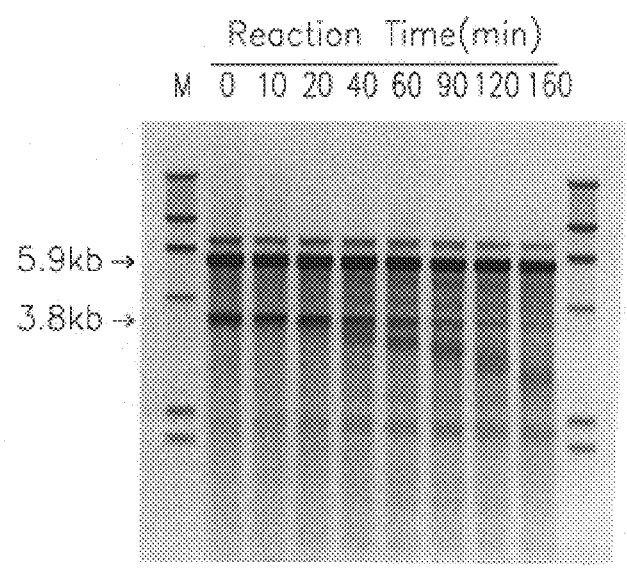

The results in FIG. 3b shows that the 3.8 kb band becomes weaker with increasing digestion time with Bal31, while the strength of the 5.9 kb band remaining constant. This suggests that the 3.8 kb fragment is relatively sensitive to exonuclease Bal31. Considering an fact that DNA at a terminal sites of the chromosome is more sensitive to the exonuclease than internal DNA of the chromosome, the 3.8 kb fragment observed for all transformants is likely a terminal DNA of the chromosome. Accordingly, it can be deduced that HARS36 of H. polymorpha is integrated into a terminal site of the chromosome in a multiple-tandem manner with 60% efficiency.

(2) Functional elements of HARS36

Figure 4:
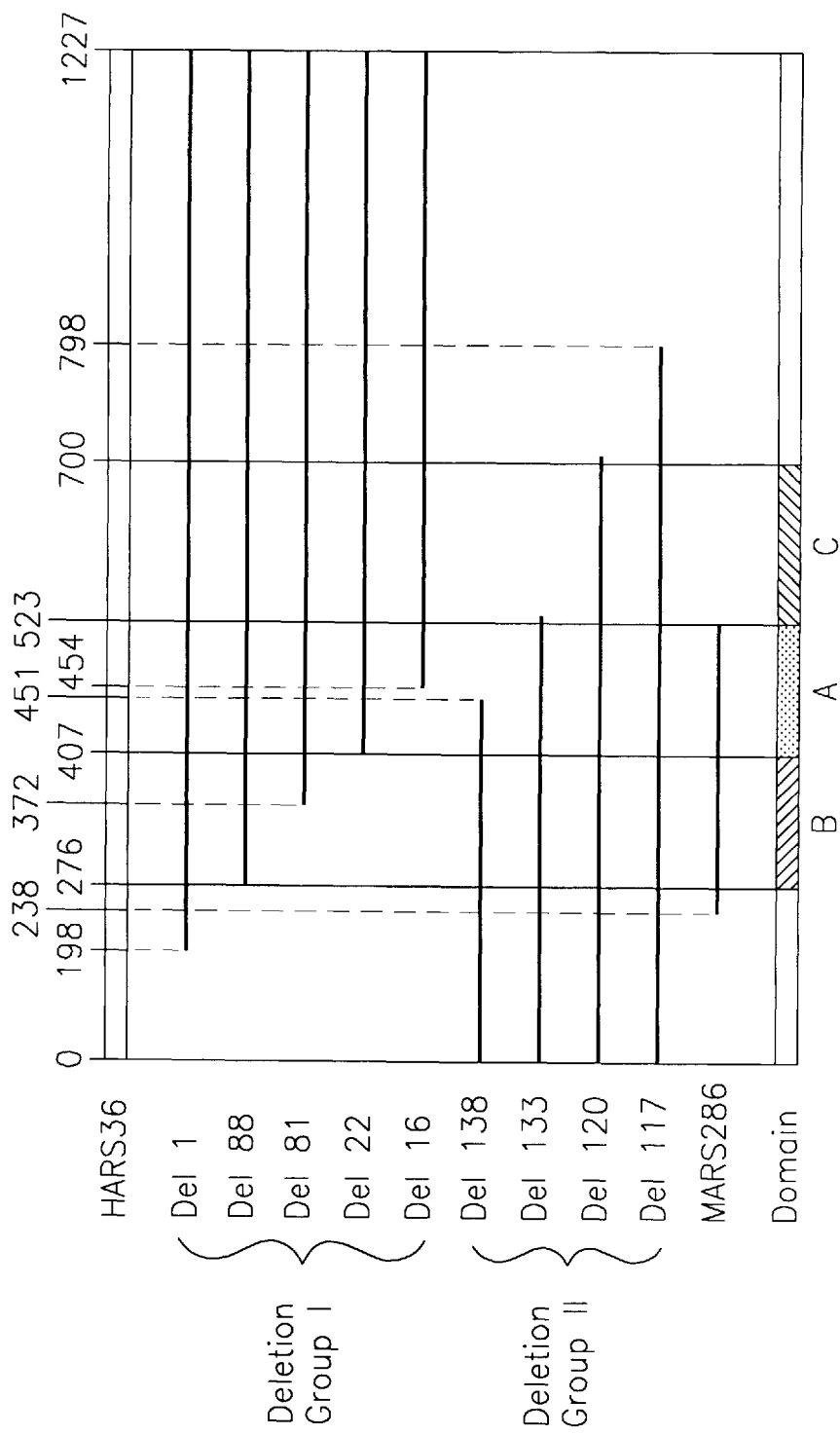
FIG. 4 depicts a schematic illustration of the deleted fragments of HARS36.

To identify functional elements of HARS36, deleted DNA fragments of HARS36 were assessed by examining the transformation efficiencies as well as the stabilities of the leucine selective marker of plasmids containing such detected fragments as follows:

1227 kb DNA of HARS was subjected to stepwise deletion from both ends using the ExoIII/Mung Bean Nuclease Deletion Kit (Stratagen Co.) to obtain two groups of deleted DNA fragments. The deletion group I consisted of DNA fragments obtained by deleting the segments starting from the 5' end to the nucleotide at position 197, 275, 371, 406 and 453 bp, respectively, and they were designated Del 1, Del 88, Del 81, Del 23 and Del 16, respectively. The deletion group II consisted of DNA fragments obtained by deleting the segments starting from the 3' end to the nucleotides at positions 452, 524, 701 and 799, respectively, and they were designated Del 138, Del 133, Del 120 and, Del 177, respectively (FIG. 4).

Each of the deleted DNA fragments obtained above was inserted in plasmid pCLHX to obtain a plasmid containing a deleted HARS36 fragment. The transformation efficiency was measured by the method of Step 5 of Example 1. The stability of the leucine selective marker of said plasmid was also measured by culturing *H. polymorpha* DL-1L(leu2) transformed by said plasmid on a minimal medium. An intact HARS36 was used as the control.

Each transformant was inoculated on a composite medium and cultured for 24 hours. The number of generations was determined by measuring the optical density of the culture solution at 600 nm. The stability of the selective marker of each generation was determined by comparing respective numbers of colonies formed on a composite medium and a minimal medium after culturing in each medium an equal number of transformants at 37° C. for 48 hours.

The result is shown in Table 2.

TABLE 2

|  | Transformation Efficiency | LEU + phenotype stability (%) |
|---|---|---|
| HARS36 | +++ | 89.1 |
| Deletion Group I |  |  |
| Del 1 | +++ | 89.9 |
| Del 88 | +++ | 89.0 |
| Del 81 | +S | 72.2 |
| Del 22 | +S | 66.2 |
| Del 16 | − | − |
| Deletion Group II |  |  |
| Del 138 | − | − |
| Del 133 | + | 76.0 |
| Del 120 | +++ | 88.8 |
| Del 117 | +++ | 89.6 |
| MARS286 | + | 76.2 |

+++: more than 2,400 transformants per 1 μg DNA
+: more than 800 transformants per 1 μg DNA
+S: more than 800 transformants per 1 μg DNA having a low growth rate
−: no transformant As compared with the control HARS36, clones Del 1 and Del 88 exhibited no significant decrease in transformation activity, while clones Del 81 and Del 22 showed reduced transformation activities as well as reduced rates of colony formation. Clone Del 16, on the other hand, had no transformation activity, suggesting that Del 16 fragment of HARS36 does not have an AR activity.

As to the deletion group II, clones Del 120 and Del 117 maintained the original transformation activity, while clone Del 133 had a diminished transformation activity, and clone Del 138, no transformation activity.

That is, the loss of the 457th to 523rd nucleotide sequences(designated "region A") entailed a complete loss of the transformation activity and the loss of the 276th to 407th nucleotide sequences(designated "region B") as well as the 523rd to the 700th(designated "region C") resulted in a reduced transformation activity and a low growth rate of the transformant, hereby reducing the HARS36 activity as a whole. Therefore, it became clear that region A plays an essential role in the HARS36 activity and region B and region C playing an additional supporting roles wherein.

To investigate the role of region C, *H. polymorpha* DL-1L(leu2) was transformed with a plasmid containing MARS286, a clone obtained from the 1227 bp HARS36 DNA to 237 bp by deleting the 5' end to the 237th nucleotide sequences and the 3' end to the 524th nucleotide sequences. The transformants were cultured on a minimal medium, total DNA of each generation was isolated, and blotted with pBC KS+ (Stratagen Co., U.S.A.) as a probe to examine how long the plasmid can be maintained at an episomal state. A plasmid pCE36 containing an intact HARS36 was used as the control.

Figure 5:
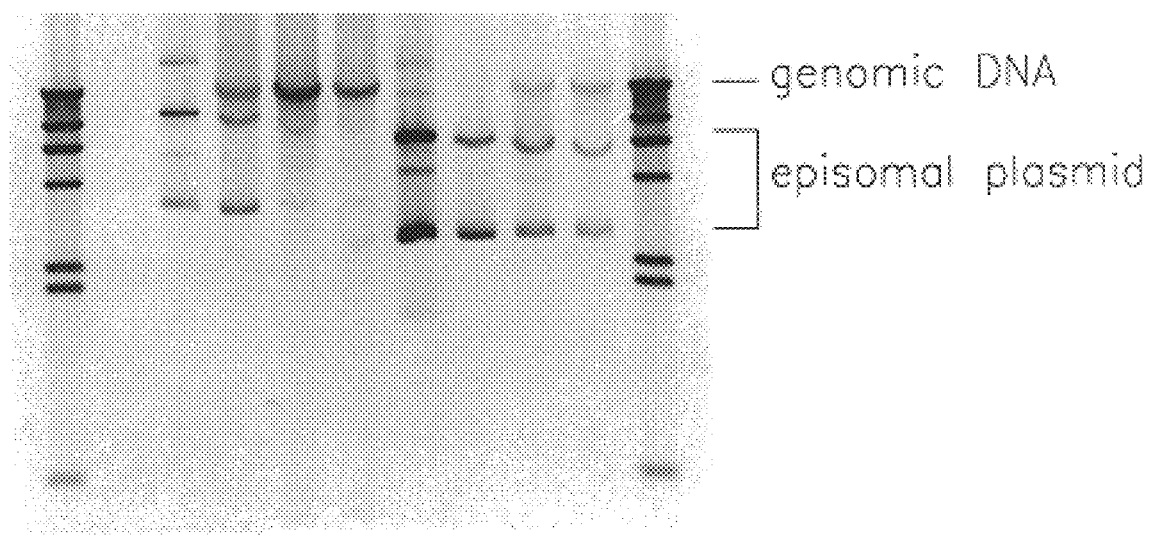
FIG. 5 represents the result of Southern blotting analysis confirming the function of C region of HARS36.

The result in FIG. 5 shows, that as compared with the control, integration of the plasmid containing the MARS286 into the chromosome became significantly inhibited. Region C is thus believed to play the role of inducing plasmid integration.

(3) Nucleotide sequence of HARS36

The nucleotide sequence of HARS36 was determined using DNA Sequencer (model 373A, Applied Biosystems Co.), and shown in SEQ ID NO:1.

Characteristic sequences were detected in the regions corresponding to functional elements. That is, an AT-rich sequence formed in the ARS core of another eucaryotes was detected in region A (the 407th to the 523th nucleotides). A repeated sequence I(RS-I) and a repeated sequence II(RS-II) of SEQ ID NOs: 8 and 9, respectively, were detected in region B (the 276th to the 407th nucleotides), and a G-rich sequence, 5'-GGGTGGCG-3', is repeated eighteen times in region C.

SEQ ID NO: 8 5'-GAATTAGAGA GG-3'
SEQ ID NO: 9 5'-GAATTAGAGC AAGTAG-3'

(4) Origin of HARS36

The genomic DNAs of *H. polymorpha* DL-1L(leu2) were digested with restriction enzymes EcoRI, HindIII, XbaI, XhoI, BamHI or PstI, and subjected to Southern blotting analysis using the whole or part HARS36 as a probe. Whole HARS36 of SEQ ID NO: 1, the 238th to the 523rd nucleotide sequences of HARS36 (covering to regions A and B), and the 992nd to the 1227th nucleotide sequences of HARS36 (covering region D) were used as probe 1, 2 and 3, respectively.

Figure 6:
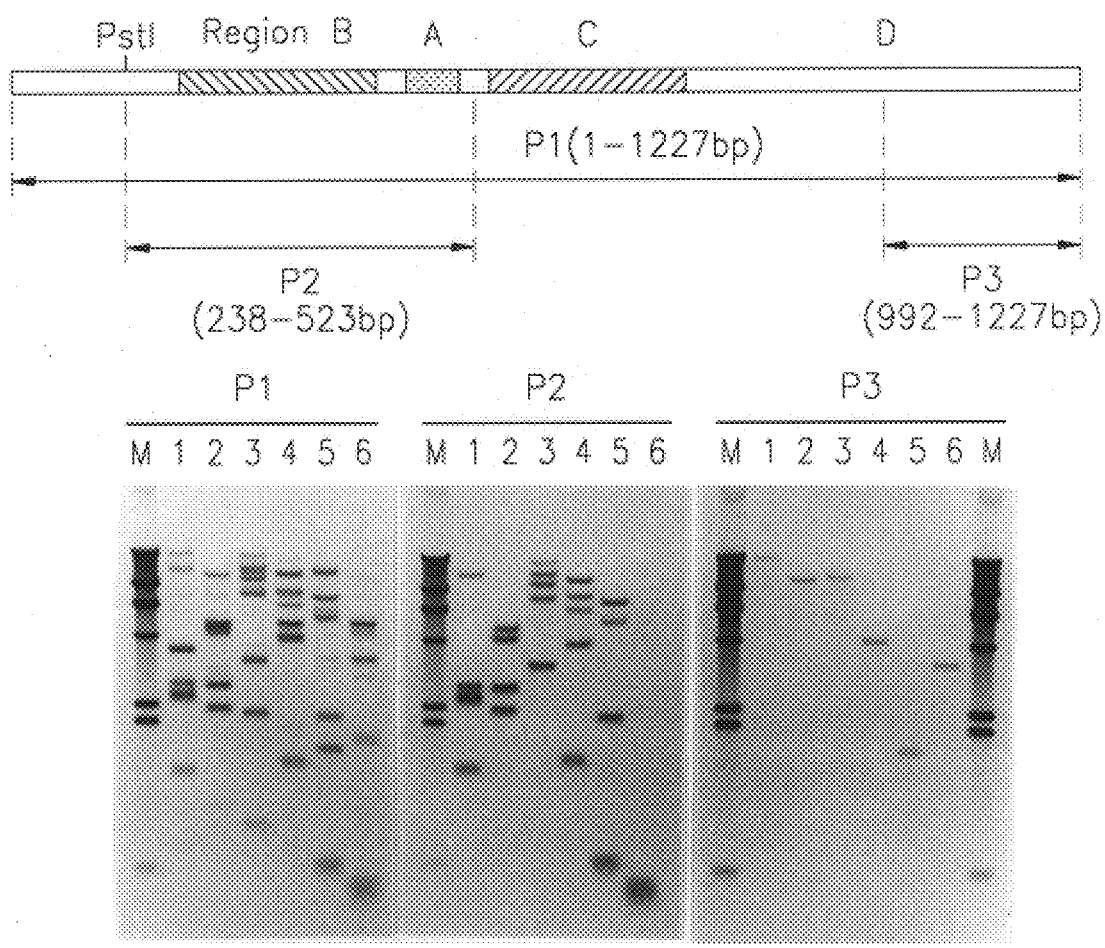
FIG. 6 displays the results of Southern blotting analyses confirming the genetic origin of HARS36.

The results are shown in FIG. 6, wherein a M lane present size markers representing 23.0, 9.4, 6.6, 4.4, 2.3, 2.2 and 0.56 kb from the top, lanes one to six correspond to genomic DNAs of *H. polymorpha* DL-1L(leu2) digested with EcoRI, HindIII, XbaI, XhoI, BamHI and PstI, respectively. As shown in FIG. 6, the probes 2 and 3 entailed different patterns of the Southern blottings, suggesting that the chromosomal origin of the region covering region A, B and C is different from that of region D. That is, HARS36 was obtained in the form of two genes complex in the cloning process.

EXAMPLE 3

TEL188, TEL135 and TEL61

Genomic DNAs of *H. polymorpha* DL-1L(leu2) was treated with T4 DNA polymerase and digested with restriction enzyme PstI to obtain a DNA fragment having a size of 400 to 600 bp. This DNA fragment was inserted into plasmid pBluescript KS+ (Stratagen Co.) at a PstI-EcoRV site, and then *E. coli* was transformed with the resultant plasmid library. Five hundred transformants were selected, and plasmid DNAs thereof were isolated and blotted with probe 2 mentioned above.

The result showed that three plasmids, designated pBKS-TEL188, pBKS-TEL135 and pBKS-TEL61, respectively, had homology with probe 2.

The three nucleotide sequences contained in the above three plasmids pBKS-TEL188, pBKS-TEL135 and pBKS-TEL61 were designated as TEL188, TEL135 and TEL61, respectively, whose nucleotide sequences were determined and registered in the GeneBank as U82170, U82171 and U82172, respectively. The nucleotide sequences of TEL188, TEL135 and TEL61 are shown in SEQ ID NOs: 2, 3 and 4, and sizes deduced therefrom were 453 bp, 405 bp and 460 bp, respectively.

The sequence of TEL188 was identical with those of regions A, B and C of HARS36, suggesting that TEL188 and regions A, B and C of HARS36 had a same chromosomal origin. The sequences of TEL135 and TEL61 were also very similar with those of regions A, B and C of HARS36, except for the occurrence of a deletion in region B of HARS36.

The termini of TEL188, TEL135 and TEL61 consisted of repeats of the sequence 5'-GGGTGGCG-3' which is identical with that of region C of HARS36, the number of repeating units being 18, 23 and 18, respectively.

E. coli DH5α cells carrying plasmid pBKS-TEL61 (E. coli DH5α/pBKS-TEL61), plasmid pBKS-TEL135 (E. coli DH5α/pBKS-TEL135) and plasmid pBKS-TEL188 (E. coli DH5α/pBKS-TEL188), respectively, were deposited on Jul 24, 1997 with the Korean Collection for Type Cultures (KCTC)(Address: KCTC, KRIBB, #52, Oun-dong, Yusong-ku, Taejon, 305-333, Republic of Korea) under the terms of the Budapest Treaty on the International Recognition of the Deposit of Microorganism for the Purpose of Patent Procedure under the accession numbers of KCTC 0353BP, KCTC 0354BP and KCTC 0355BP.

EXAMPLE 4
AR activities of TEL188, TEL135 and TEL61

Activities of TEL188, TEL135 and TEL61 obtained in Example 3 were examined as follows:

TEL188, TEL135 and TEL61 were successively inserted in plasmid pCLHX in PstI-HindIII position to obtain plasmids pCTEL188, pCTEL135 and pCTEL61, respectively, and then H. polymorpha DL-1L(leu2) was transformed with each of the plasmids thus obtained to measure the transformation efficiency as in step 5 of Example 1. Plasmid pCLHX containing no ARS and plasmid pCE36 containing HARS36 were used as controls.

The results are shown in Table 3.

TABLE 3

| Plasmid | Inserted ARS | Number of Transformants/ μg DNA |
| --- | --- | --- |
| pCLHX | — | 5 |
| pCE36 | HARS36 | 2950 |
| pCTEL188 | TEL188 | 2920 |
| pCTEL135 | TEL135 | 2200 |
| pCTEL61 | TEL61 | 2870 |

As shown in Table 3, TEL188, TEL135 and TEL61 had similar transformation efficiencies and were functionally identical with HARS36. It is thus confirmed that the autonomously replicating sequences as well as the multiple repeats of sequence, 5'-GGGTGGCG-3', found in all of HARS36, TEL188, TEL135 and TEL61, are responsible for the occurrence of multiple-tandem integration.

EXAMPLE 5
GAPDH gene of H. polymorpha

Synthetic primers 1 and 2 were prepared based on the sequence of glyceraldehyde-3-phosphate dehydrogenase (GAPDH) gene of S. cerevisiae (Holland et al., J. Biol. Chem., 254, 9839(1979)).

primer 1: 5'-AAGCTTACCA GTTCTCACAC GG-3' (SEQ ID NO: 10)
primer 2: 5'-AAGCTTACAA TCAATGAATC GA-3' (SEQ ID NO: 11)

Polymerase chain reaction was conducted using primers to isolate GAPDH gene of S. cerevisiae (Sc-GAPDH gene) from chromosomal DNA of S. cerevisiae 2805.

The Sc-GAPDH gene was then inserted in plasmid pT7-Blue T-vector (Novagen Co.) to prepare plasmid pT7-SGAP2 containing Sc-GAPDH gene.

Chromosomal DNAs of H. polymorpha DL-1L(leu2) were isolated and then digested with a restriction enzyme BamHI. Plasmid pT7-SGAP2 obtained above was cut with restriction enzyme XbaI. The digested chromosomal DNAs were blotted with plasmid pT7-SGAP2 labeled with DIG as a probe to obtain a band having a size of about 14 kb.

Chromosomal DNAs of H. polymorpha DL-1L(leu2) were digested with restriction enzyme BamHI. Twelve to sixteen kb DNA fragments thereof were isolated and inserted in plasmid pBluescript KS+ (Stratagen Co.) cleaved with restriction enzyme BamHI to prepare a genomic library.

Figure 7:
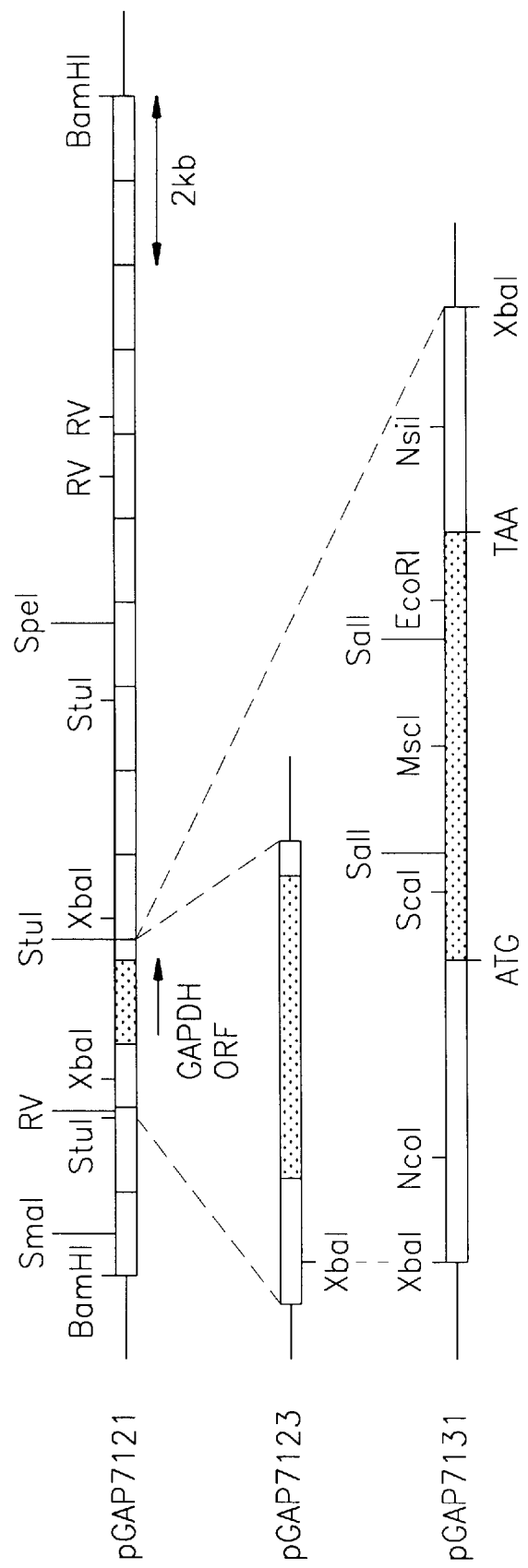
FIG. 7 exhibits the restriction enzyme maps of plasmids pGAP7121, pGAP7123 and pGAP7131.

E. coli was transformed with the genomic library to obtain 1×10⁴ transformants. DNAs of the transformants were isolated and blotted with Sc-GAPDH labeled with DIG as a probe to clone plasmid pGAP7121 containing GAPDH gene of H. polymorpha (Hp-GAPDH gene). A restriction map of plasmid pGAP7121 is shown in FIG. 7.

The plasmid pGAP7121 was cleaved with restriction enzyme StuI to obtain a DNA fragment containing Hp-GAPDH gene, and the DNA fragment was inserted in plasmid pBluescript KS+ cut with restriction enzyme EcoRV to subclone plasmid pGAP7123.

On the other hand, plasmid pGAP7121 was cleaved with restriction enzyme XbaI to obtain another DNA fragment containing Hp-GAPDH gene, and the DNA fragment was inserted in plasmid pBluescript KS+ cut with restriction enzyme XbaI to subclone plasmid pGAP7131.

The nucleotide sequence of Hp-GAPDH gene contained in plasmid pGAP7131 was determined using ABI Prism Dye Terminator Cycle Sequencing Ready Reaction Kit (Perkin-Elmer) and DNA sequencer (Model 373A, Applied Biosystem). The nucleotide sequence of Hp-GAPDH gene is shown in SEQ ID NO: 5, and registered at GeneBank as U95625 on Mar. 28, 1997.

The amino acid sequence deduced from the nucleotide sequence of Hp-GAPDH has a high sequence similarity of 72% with that of Sc-GAPDH.

EXAMPLE 6
Hp-GAPDH promoter

A polymerase chain reaction of plasmid pGAP7123 prepared in the Example 5 was conducted using synthetic primers 3 and 4 to obtain a 798 bp DNA fragment of SEQ ID NO: 7 containing Hp-GAPDH promoter.

primer 3: 5'-GAATTCGAAT ATTGTTTCTA TATTATC-3' (SEQ ID NO: 12)
primer 4: 5'-GTAAAACGAC GGCCAGT-3' (SEQ ID NO: 13)

EXAMPLE 7
Characteristic of Hp-GAPDH promoter

The Hp-GAPDH promoter obtained in Example 6 was inserted in plasmid pT7-Blue T-vector (Novagen Co.) to obtain plasmid pT7-HGAP.

YEGα-HIR525 (Sohn et al., Process Biochem., 30, 563 (1995)) was cut with restriction enzymes EcoRI and SalI to obtain a DNA fragment containing a pre-pro leader secretory signal of mating factor α in Saccharomvces cerevisiae and a hirudin gene. The plasmid pGAP7131 prepared in Example 5 was cut with restriction enzymes SalI and XbaI to obtain a DNA fragment containing a Hp-GAPDH terminator. The DNA fragments thus obtained were inserted in plasmid pT7-HGAP to prepare plasmid pT7-GAPHIR containing an expression cassette of hirudin.

Figure 8:
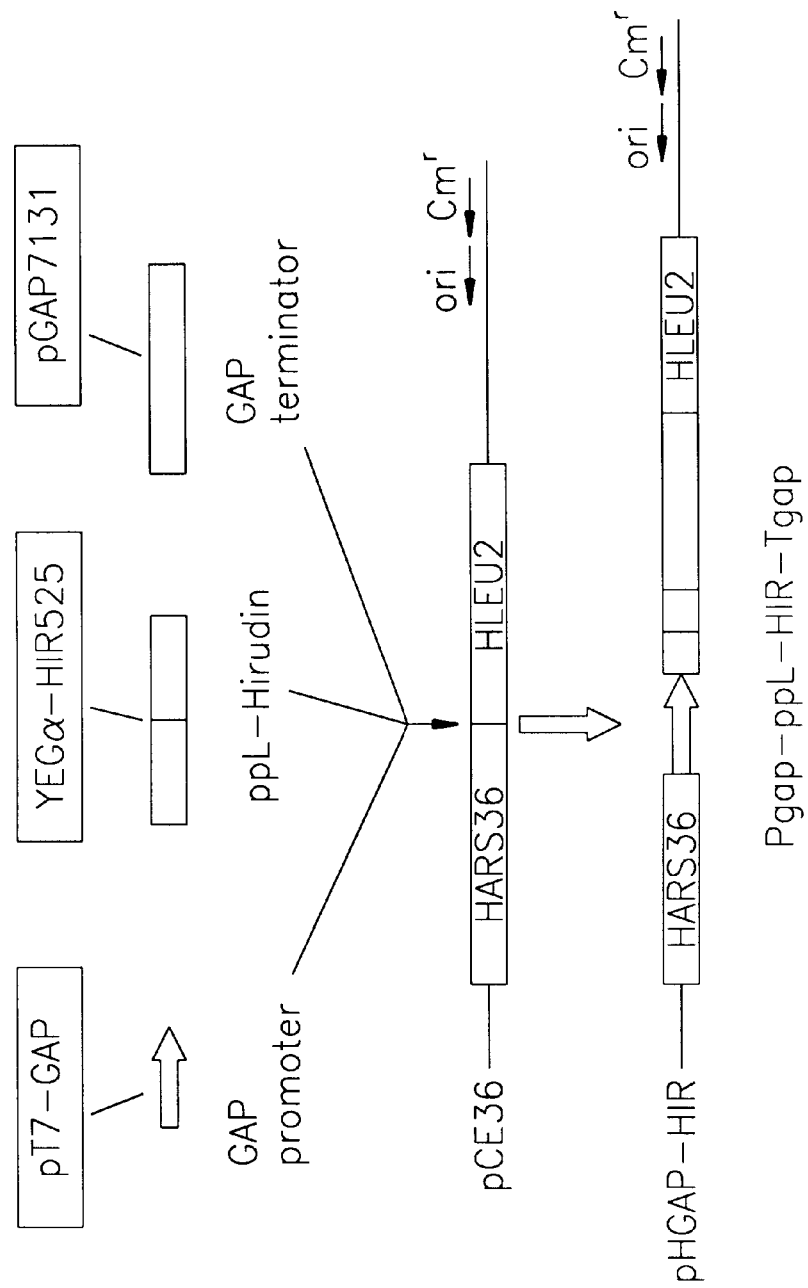
FIG. 8 shows a schematic diagram for constructing plasmid pHGAP-HIR.

The plasmid pT7-GAPHIR was cut with restriction enzymes BamHI and HindIII and blunted with a Klenow DNA polymerase to obtain a DNA fragment containing an expression cassette. The DNA fragment thus obtained was inserted into plasmid pCE36 prepared in (Step 4) of Example 1, which has been cut with restriction enzyme EcoRI and blunted with Klenow DNA polymerase, to prepare plasmid pHGAP-HIR (FIG. 8).

H. polymorpha DL-1L(leu2) was transformed with plasmid pHGAP-HIR and the resultant transformant was subjected to a stabilization procedure on YPD medium (1% yeast extract, 2% Bacto-peptone, 2% glucose) for 50 generations and, then, stabilized colonies were selected in the minimal medium. H. polymorpha DL-1L(leu2) carrying plasmid pHGAP-HIR (H. polymorpha DL-1L/pHGAP-HIR) was deposited on Jul. 24, 1997 with the Korean Collection for Type Cultures (KCTC) (Address: KCTC, KRIBB, #52, Oun-dong, Yusong-ku, Taejon, 305-333, Republic of Korea) under the terms of the Budapest Treaty on the International Recognition of the Deposit of Microorganism for the Purpose of Patent Procedure under the accession number of KCTC 0357BP.

About ten stabilized transformants were cultured in YPD medium and the amount of hirudin secreted in the culture solution was quantified. For the quantification of hirudin, human thrombin was diluted in a thrombin reaction buffer (0.1M Tris-HCl (pH 8.0), 0.12M sodium chloride, 0.001% sodium azide and 0.1% bovine serum albumin) to a concentration of 0.6 NIH U/ml, while Chromozym TH (Boehringer Mannheim Co.), which is an artificial substrate of thrombin, was dissolve in a thrombin reaction buffer to a concentration of 200 μM. A hirudin standard (Accurate Chemical & Scientific Co.) was diluted in a thrombin reaction buffer to prepare standard solutions having concentrations of 0, 0.1, 0.2, 0.3, 0.4, 0.5 and 0.6 ATU (antithrombin unit)/ml, wherein 1 ATU is an amount of hirudin to completely inhibit one NIH unit of human thrombin. 50 μl each of the culture solutions diluted in 50 μl of a thrombin solution was added to each well of a 96-well microtiter plate, and then 100 μl of Chromozym TH solution was added to each well. The optical density at 405 nm was measured for five minutes using the ELISA reader (THERMOmax, Molecular Devices) to determine the rate of optical density increase. The amount of hirudin in a culture solution was determined by comparing the above rate of optical density increase with that of a standard hirudin solution.

The result is shown in Table 4.

TABLE 4

| Transformant | 1 | 2 | 3 | 4 | 5 |
|---|---|---|---|---|---|
| Hirudin (mg/l) | 1.7 | 2.3 | 0.9 | 1.4 | 0.9 |
| Transformant | 6 | 7 | 8 | 9 | 10 |
| Hirudin (mg/l) | 3.4 | 2.9 | 3.2 | 2.7 | 1.9 |

Sixth transformants which were most active in the production of hirudin among the ten transformants examined, were cultured for thirty hours in three separate YP mediums (1% yeast extraction and 2% bactopeptone) containing 2% glucose, 2% glycerol and 2% methanol, respectively. The amount of hirudin in each culture solution was quantified as above.

The dependency of hirudin productivity on the carbon source is shown in Table 5.

TABLE 5

| Carbon Source | Cell Conc. ($OD_{600}$) | Total hirudin (mg/l) | Productivity (mg/l/H) |
|---|---|---|---|
| Glucose | 55.3 | 13.4 | 0.45 |
| Glycerol | 41.0 | 17.6 | 0.59 |
| Methanol | 17.2 | 3.7 | 0.12 |

As shown in Table 5, the hirudin gene was expressed in all transformants cultured in the presence of various carbon sources. The transformant cultured in glucose or glycerol showed a growth rate and hirudin productivity which are higher than that observed in methanol by a factor of 3 and 5, respectively.

EXAMPLE 8

Preparation of plasmid pGLG578

A plasmid pGLG578 containing TEL188, LEU2 gene, GAPDH promoter and APH gene was prepared as follows:

(Step 1) Preparation of plasmid PBLT188

Plasmid pCE36 prepared in (Step 4) of Example 1, which contained a LEU2 gene, was cut with restriction enzymes BamHI and XbaI to obtain a DNA fragment containing the LEU2 gene. The DNA fragment thus obtained was inserted in plasmid PBKS-TEL188 prepared in Example 3 at the BamHI-XbaI position to prepare plasmid PBLT188 containing TEL188 and the LEU2 gene.

(Step 2) Preparation of plasmid pGL418

Figure 9:
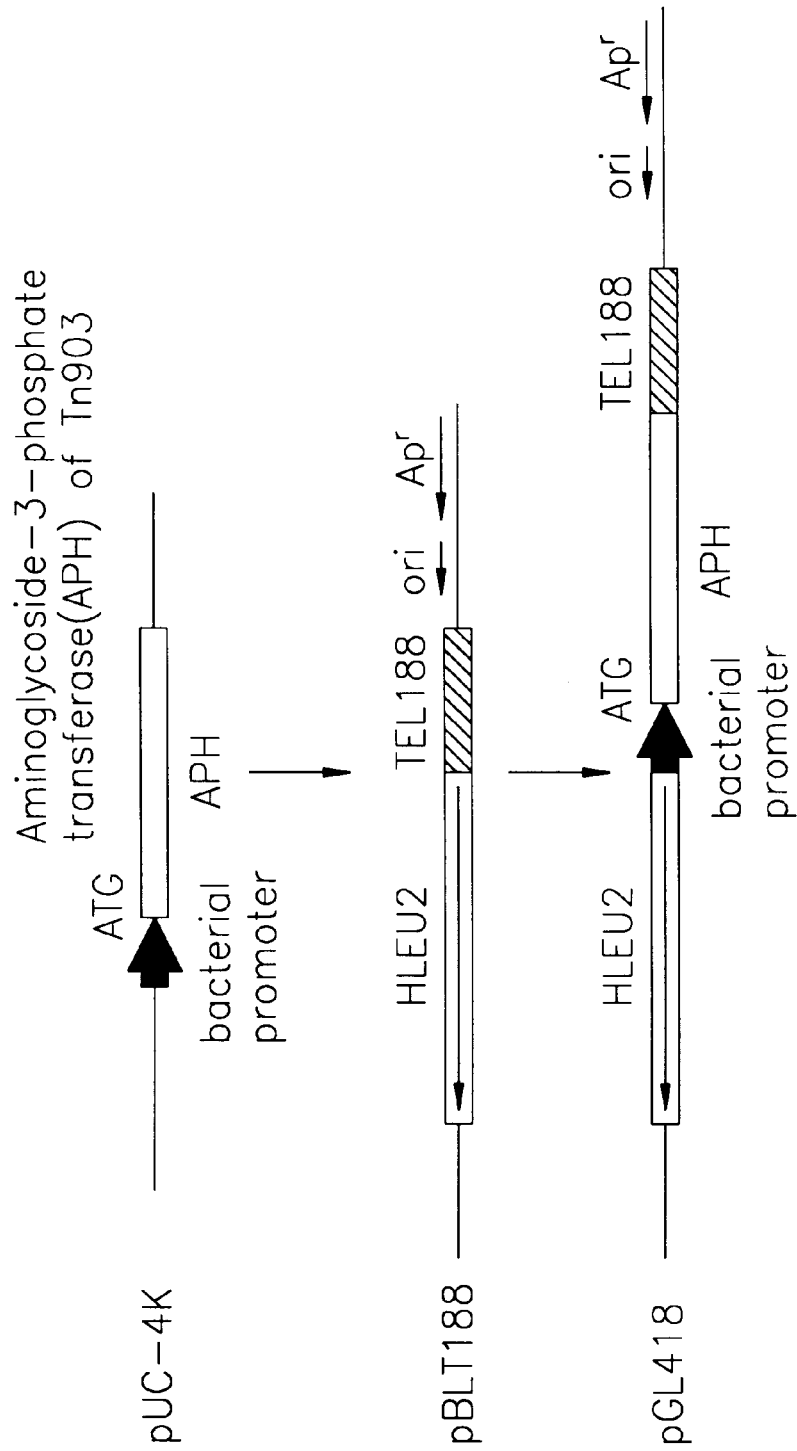
FIG. 9 illustrates the structures of plasmids pUC-4K, pBLT188 and pGL418.

Plasmid pUC-4K (Pharmacia Co.) which contained an aminoglycoside 3-phosphate transferase(APH) gene of E. coli transposon Tn903, was cut with restriction enzyme PstI. The DNA fragment thus obtained was inserted in plasmid PBLT188 which had been cleaved with PstI to prepare plasmid pGL418 containing TEL188, LEU2 gene and APH gene (FIG. 9).

(Step 3) Preparation of plasmid pGLG578

A polymerase chain reaction was conducted using plasmid pUC-4K (Pharmacia Co.) as a template and synthetic primers 5 and 6 to obtain an APH gene.

primer 5: 5'-GAATTCGTTA TGAGCCATAT TCAA-3' (SEQ ID NO: 14)

primer 6: 5'-GTAAAACGAC GGCCAGT-3' (SEQ ID NO: 13)

Figure 10:
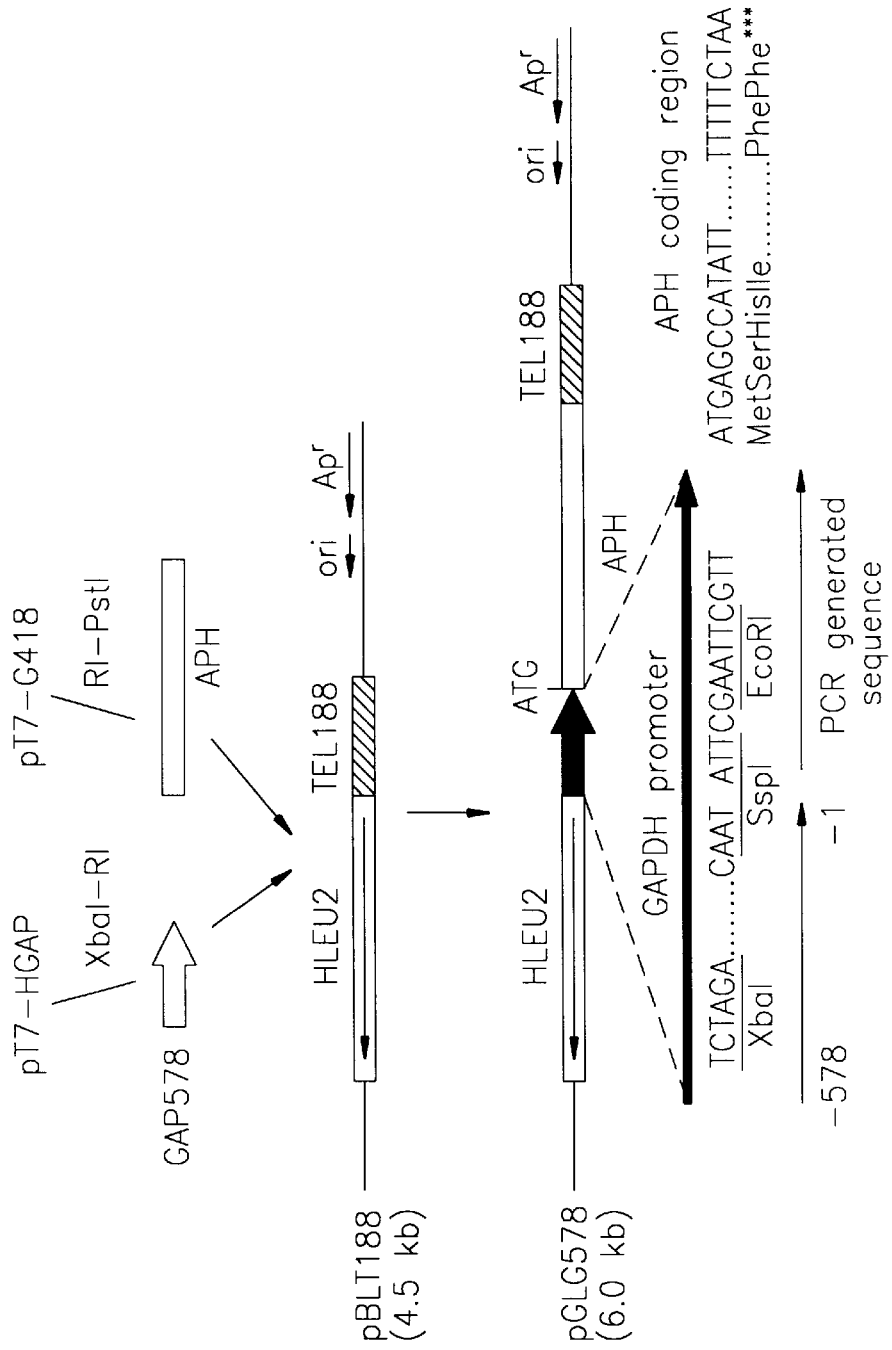
FIG. 10 presents a schematic illustration of the structures of plasmids PBLT188 and pGLG578.

The APH gene was then integrated into plasmid pT7-Blue T-vector (Novagen Co.) at the EcoRV site to prepare plasmid pT7G418, which was cut with restriction enzymes EcoRI and PstI to obtain a DNA fragment of about 1 kb containing the APH gene. Plasmid pT7-HGAP prepared in Example 7 was cut with restriction enzymes XbaI and EcoRI to obtain a 578 bp DNA fragment having Hp-GAPDH promoter activity, which corresponded to the 219th to 796th nucleotides of SEQ ID NO: 7. Two DNA fragments thus obtained were inserted concurrently into XbaI-PstI site of plasmid PBLT188 to prepare plasmid pGLG578 containing a fusion gene of Hp-GAPDH promoter and APH gene (FIG. 10).

EXAMPLE 9

Operation of APH promoter of E. coli in H. polymorpha

H. polymorpha DL-1L(leu2) was transformed with plasmid pGL418 prepared in (Step 2) of Example 8 at an efficiency of $2 \times 10^3$ transformants/μg DNA, and cultured on a minimal medium to select transformants. The selected transformants were combined, inoculated and cultured in 50 ml of YPD medium until fifty generations. A portion of the transformants was taken from the culture solution at regular interval, and cultured on a minimal medium to determine the growth rate at a given time. When a constant growth rate between colonies was observed, the transformant was deemed completely stabilized.

1×10⁵ cells were spread on YPD and minimal media, cultured for one week, and the number of colonies formed was measured to determine the degree of stabilization after 50 generations. Also, 1×10⁵ cells were spread on each of six minimal media containing antibiotic G418 at a concentration of 0, 0.3, 0.5, 1.0, 2.0, 3.0 or 4.0 mg/ml, respectively, and cultured for one week to measure the number of colonies resistant to G418. Plasmid PBLT188 prepared in (Step 1) of Example 8 was employed as a control.

The result is shown in Table 6.

TABLE 6

| Plasmid | A* | B* | C* | Conc. of G418 (mg/ml) | | | | | |
|---|---|---|---|---|---|---|---|---|---|
| | | | | 0.3 | 0.5 | 1.0 | 2.0 | 3.0 | 4.0 |
| | | | | Number of resistant transformants | | | | | |
| pBLT188 | 6.9 | 1.7 | 2.5 | 2 | 0 | 0 | 0 | 0 | 0 |
| pGL418 | 6.9 | 1.7 | 2.6 | 19 | 16 | 16 | 12 | 9 | 4 |

A*: Number of cells initially inoculated (× 10⁴)
B*: Number of stabilized cells (× 10³)
c*: Degree of stabilization (%)

As shown in Table 6, the transformants containing plasmid PBLT188 did not survive at 0.5 mg/ml of G418, while transformants containing plasmid pGL418 survived even at 4 mg/ml of G418 and grew slowly to form a colony after one week.

The genomic DNAs were isolated from the transformants, digested with restriction enzyme SmaI, and subjected to Southern blotting analysis by employing DIG-labeled LEU2 gene as a probe.

Figure 11A:
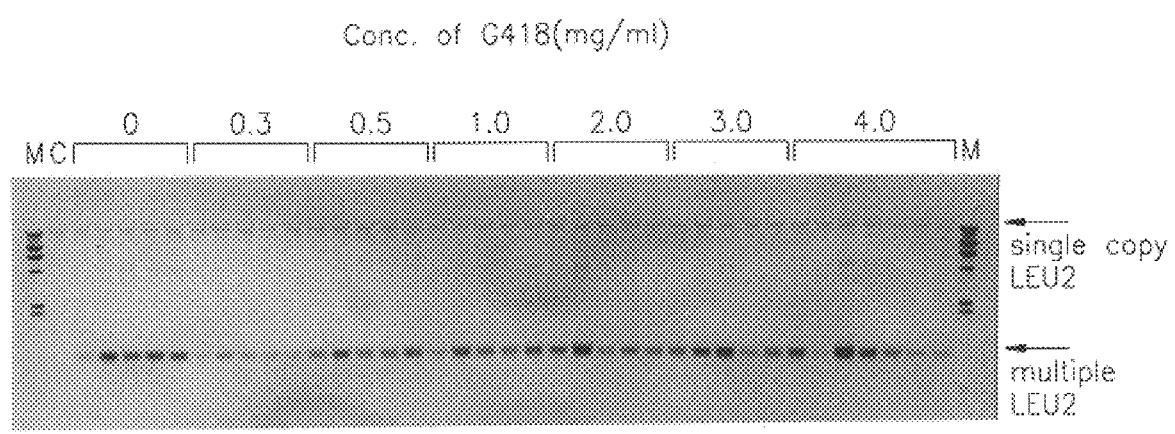
FIGS. 11A, 11B and 11C indicate the result of Southern blotting analysis confirming the transformation of G418-resistant transformants containing plasmids pGL418, pGLG578 and pGLG61, respectively.
Figure 11B:
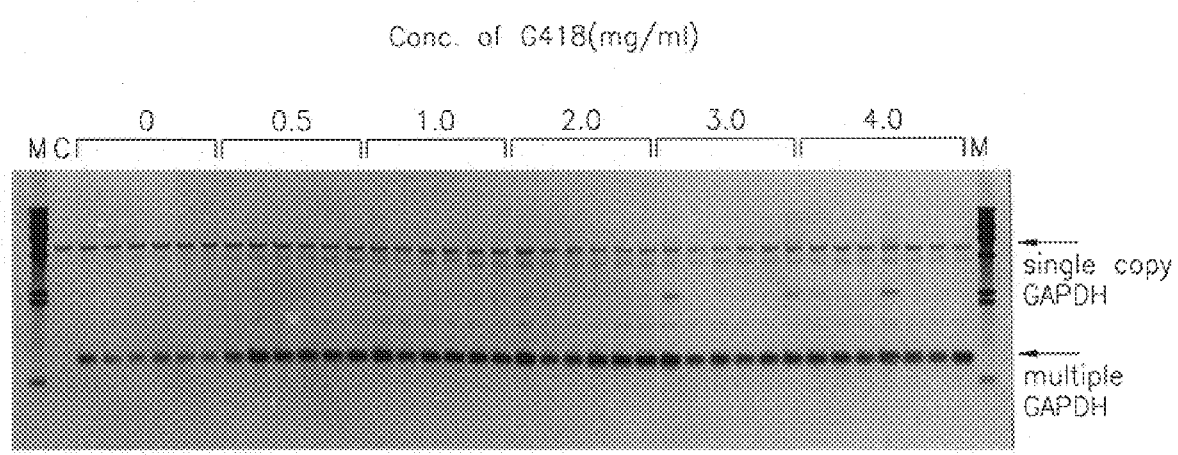

The result is shown in FIG. 11, wherein the single LEU2 gene originating from the host itself appears at 30.0 kb position and the multiple LEU2 genes originating from the plasmid are shown at about 1.0 kb position. This result thus confirms that *H. polymorpha* DL-1L(leu2) had been transformed by plasmid pGL418.

Although increased copies of a LEU2 gene were observed in some part of the G418-resistant transformants, as compared with a control selected only by the leucine selective marker, such increase was found to be independent of the G418 concentration, and other transformants did not contain more copies of LEU2 gene than a control, indicating that the resistance to G418 thereof resulted from spontaneous mutation.

This result suggests that the promoter originating from *E. coli* did not function properly in *H. polymorpha*. Therefore, the APH gene derived from *E. coli* transposon Tn903 under the control of an *E. coli* promoter is not an efficient selective marker in *H. polymorpha*.

EXAMPLE 10

G418 resistance of fusion gene

*H. polymorpha* DL-1L(leu2) was transformed with plasmid pGLG578 prepared in (Step 3) of Example 8, subjected to a stabilization procedure, and the degree of stabilization after fifty generations as well as the number of G418-resistant colonies were measured by repeating the procedure of Example 9 except that the duration of culture was 48 hours instead of one weak. Plasmids PBLT188 and pGL418 prepared in (Step 1) and (Step 2) of Example 8, respectively, were used as controls.

The result is shown in Table 7.

TABLE 7

| Plasmid | A* | B* | C* | Conc. of G418 (mg/ml) | | | | | |
|---|---|---|---|---|---|---|---|---|---|
| | | | | 0.3 | 0.5 | 1.0 | 2.0 | 3.0 | 4.0 |
| | | | | Number of resistant transformants | | | | | |
| pBLT188 | 6.9 | 1.7 | 2.5 | 2 | 0 | 0 | 0 | 0 | 0 |
| pGL418 | 6.9 | 1.7 | 2.6 | 19 | 16 | 0 | 0 | 0 | 0 |
| pGLG578 | 11.1 | 1.7 | 1.5 | 1280 | 1070 | 624 | 410 | 307 | 233 |

A*: Number of cells initially inoculated (× 10⁴)
B*: Number of stabilized cells (× 10³)
c*: Degree of stabilization (%)

As shown in Table 7, transformants containing the plasmids PBLT188 and pGL418 did not grow at 1.0 mg/ml of G418 for 48 hours, while transformants containing plasmid pGLG578 grew rapidly at 4 mg/ml of G418 and the G418-resistance thereof was dependent on the G418 concentration.

The above result suggested that a gene obtained by fusing Hp-GAPDH promoter and *E. coli* APH gene may be used as an effective selective marker.

For the purpose of confirming the relationship between the resistance to G418 and the copy number of introduced gene in the *H. polymorpha* DL-1L(leu2) transformants containing plasmid pGLG578 prepared in Example 8, six transformants containing the plasmid were randomly selected at various concentrations of G418. The genomic DNAs were isolated from the transformants, digested with restriction enzyme XhoI, and subjected to Southern blotting analysis by employing DIG-labeled Hp-GAPDH promoter as a probe.

Figure 12:
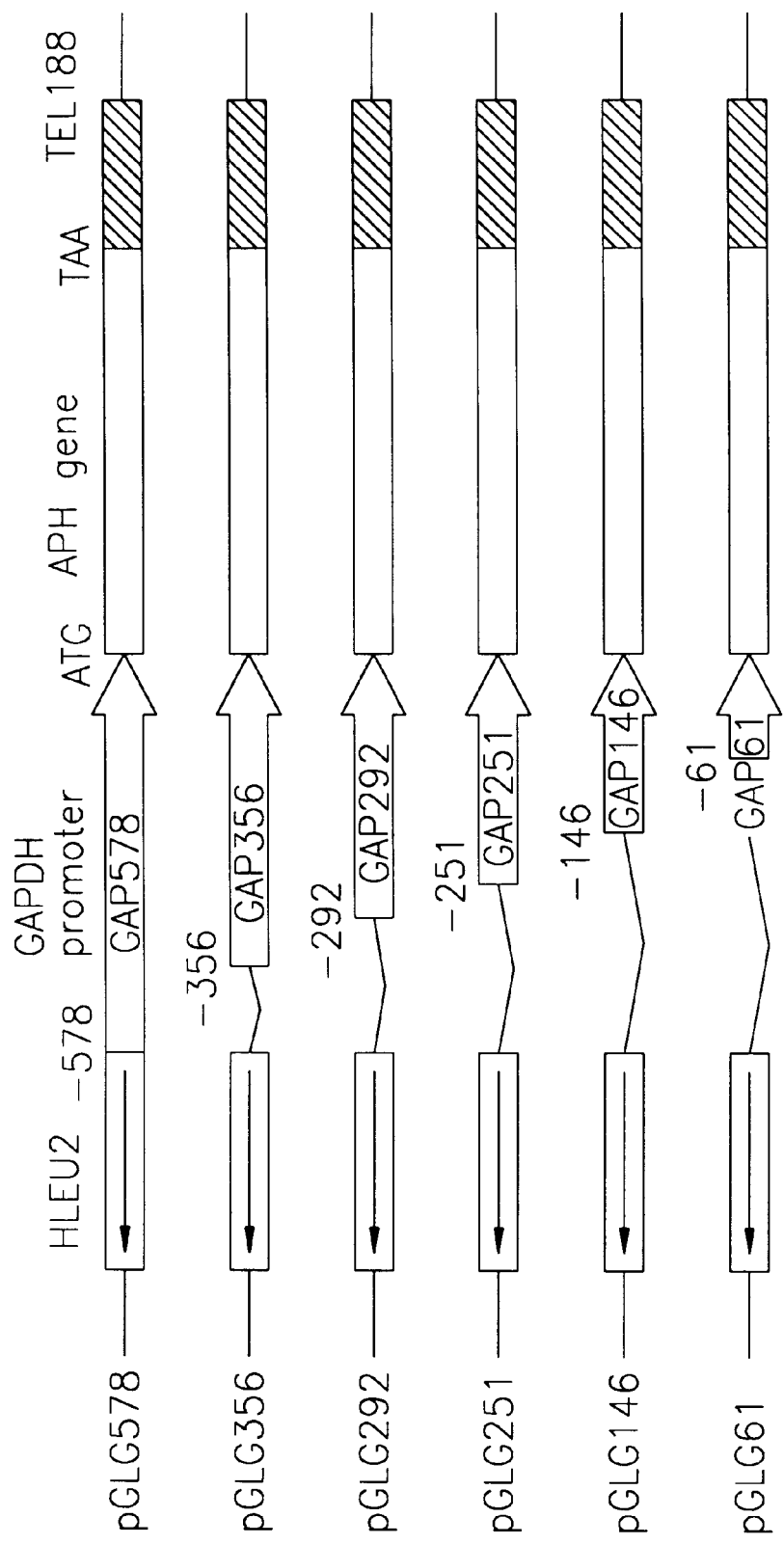
FIG. 12 displays a schematic illustration of the structures of plasmids pGLG578, pGLG356, pGLG292, pGLG251, pGLG146 and pGLG61.

The result is shown in FIG. 12, wherein the single Hp-GADPH promoter originating from the host itself is shown at 5.5 kb position and the multiple Hp-GADPH promoter originating from the plasmid appears at about 0.7 kb position.

On the other hand, for the purpose of determining the copy number of the integrated gene as function of the G418 concentration, the genomic DNAs of the transformants containing pGLG578 in FIG. 12 were 10-fold diluted with TE buffer (10 mM Tris, 1 mM EDTA, pH 7.5), and subjected to Southern blotting analysis by employing DIG-labeled Hp-GAPDH promoter as a probe. The integration copy numbers were determined by the image analyzer with respect to their signal intensities.

The result is shown in Table 8.

TABLE 8

| Concentration of G418 (mg/ml) | 0 | 0.5 | 1.0 | 2.0 | 3.0 | 4.0 |
|---|---|---|---|---|---|---|
| Copy number | 1.0 | 8.2 | 10.2 | 14.4 | 13.5 | 12.5 |

As shown in Table 8, about fifteen copies of the introduced gene were found at 2 mg/ml of G418, while the copy number did not increase at beyond 2 mg/ml of G418. The G418 resistance at a concentration of more than 2 mg/ml may be attributed to the strong activity of the Hp-GAPDH promoter.

EXAMPLE 12

Preparation of plasmid containing deleted Hp-GAPDH promoter

Figure 13:
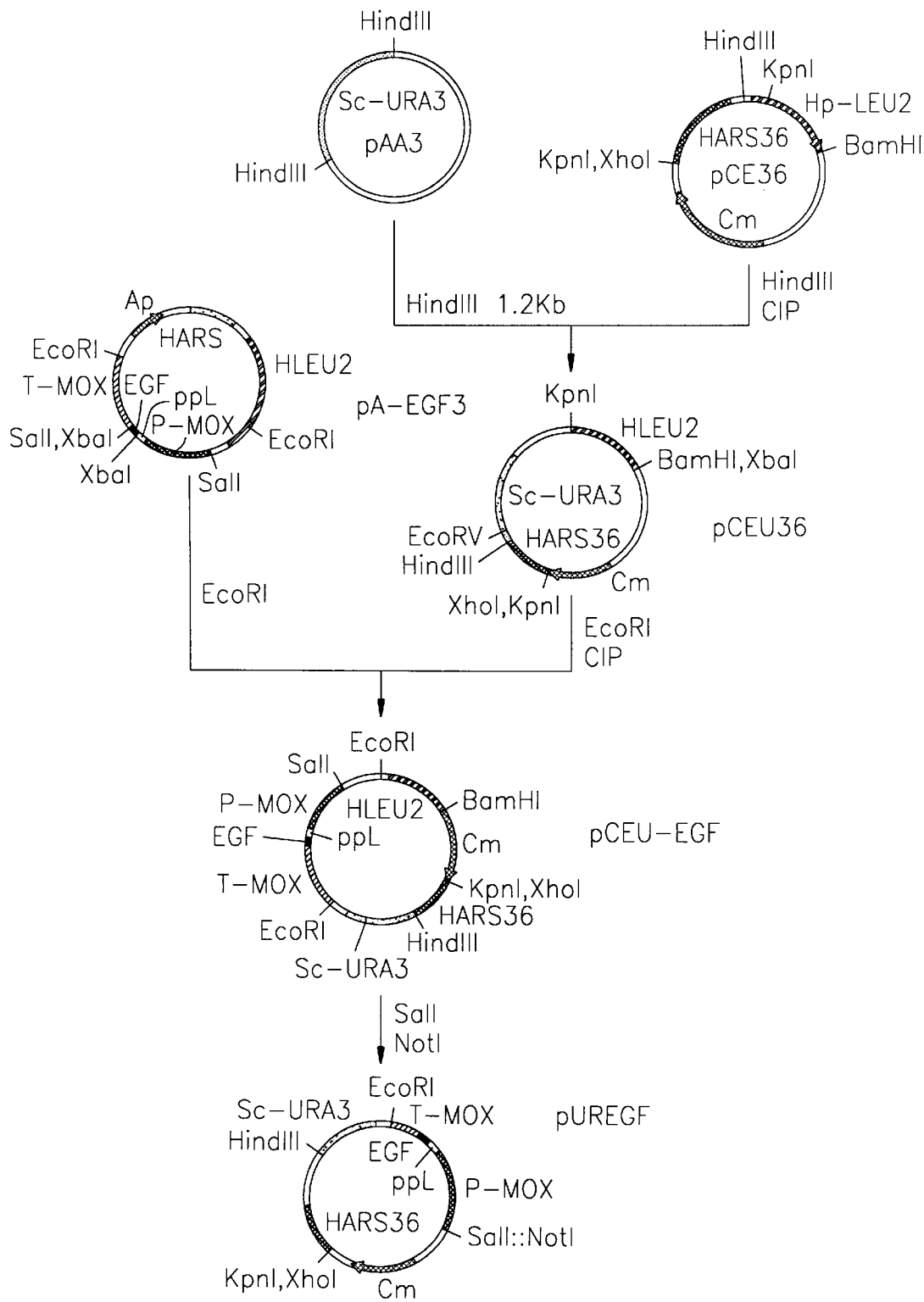
FIG. 13 delineates a schematic diagram for constructing an expression vector pUREGF for expressing human epidermal growth factor (hEGF) in *Hansenula polymorpha*.

To increase the copy number of a transforming plasmid by way of reducing promoter activity, the Hp-GAPDH promoter was deleted as follows:

20 μg of plasmid pGAP7123 prepared in Example 5, which contained a Hp-GAPDH promoter, was digested with restriction enzyme NotI and both ends thereof were filled with α-thio DNTP by using Klenow DNA fragment to make blunt ends. The resulting DNA was further digested with restriction enzyme BamHI. The DNA fragment thus obtained was deleted stepwise from the 5'-end using the ExoIII/Mung Bean Nuclease Deletion Kit (Stratagen Co.). As a result of a sequence analysis of deleted DNA fragments, deleted Hp-GAPDH promoters having 441st–796th(GAP356), 505th–796th(GAP292), 546th–796th(GAP251), 651st–796th(GAP146) and 736th–796th(GAP61) nucleotides of SEQ ID NO: 7, respectively, were obtained. Plasmids pGLG356, pGLG292, pGLG251, pGLG146 and pGLG61 containing a APH gene and a deleted Hp-GAPDH promoter of above, respectively, were prepared according to the procedure of (Step 3) of Example 8 (FIG. 13).

H. polymorpha DL-1L(leu2) was transformed with each plasmid, subjected to a stabilization procedure and cultured on a YPD medium and a minimal medium with or without G418 for 48 hours to measure the degree of stabilization and G418 resistance.

The result is shown in Table 9.

TABLE 9

| Plasmid | A* | B* | C* | Conc. of G418 (mg/ml) | | | | | |
|---|---|---|---|---|---|---|---|---|---|
| | | | | 0.3 | 0.5 | 1.0 | 2.0 | 3.0 | 4.0 |
| | | | | Number of resistant transformants | | | | | |
| pGLG578 | 11.1 | 1.7 | 1.5 | 1280 | 1070 | 624 | 410 | 307 | 233 |
| pGLG356 | 8.9 | 1.9 | 2.1 | 1580 | 1320 | 982 | 564 | 415 | 295 |
| pGLG292 | 8.0 | 3.6 | 4.5 | 3040 | 2560 | 1970 | 1450 | 1020 | 847 |
| pGLG251 | 6.8 | 2.5 | 3.7 | 1860 | 1780 | 1425 | 1100 | 894 | 698 |
| pGLG146 | 6.9 | 3.2 | 4.6 | 2150 | 1060 | 602 | 306 | 223 | 165 |
| pGLG61 | 7.1 | 5.4 | 7.6 | 802 | 253 | 53 | 32 | 30 | 23 |

A*: Number of cells initially inoculated ($\times 10^4$)
B*: Number of stabilized cells ($\times 10^{3)}$
c*: Degree of stabilization (%)

As can be seen from Table 9, the resistance of the transformants to G418 did not decrease when the 1st to the 650th nucleotides of the GAPDH promoter having the nucleotide sequence of SEQ ID NO: 7 had been deleted, while the resistance of the transformants to G418 decreased when the 1st to 735th nucleotides of the GAPDH promoter having the nucleotide sequence of SEQ ID NO: 7 had been deleted.

Accordingly, it was confirmed that GAP61 is suitable as a promoter for APH gene for the selection of transformants having high copy of integrated plasmid.

EXAMPLE 13
Property of plasmid containing deleted GAPDH promoter

For the purpose of examining the relation between the resistance to G418 and the copy number of introduced gene in the H. polymorpha DL-1L(leu2) transformants containing the plasmids prepared in Example 12, transformants containing each of said plasmids were randomly selected at various concentrations of G418. The genomic DNAs were isolated from the transformants, digested with restriction enzyme SmaI, and subjected to Southern blotting analysis by employing DIG-labeled LEU2 gene as a probe.

Figure 11C:
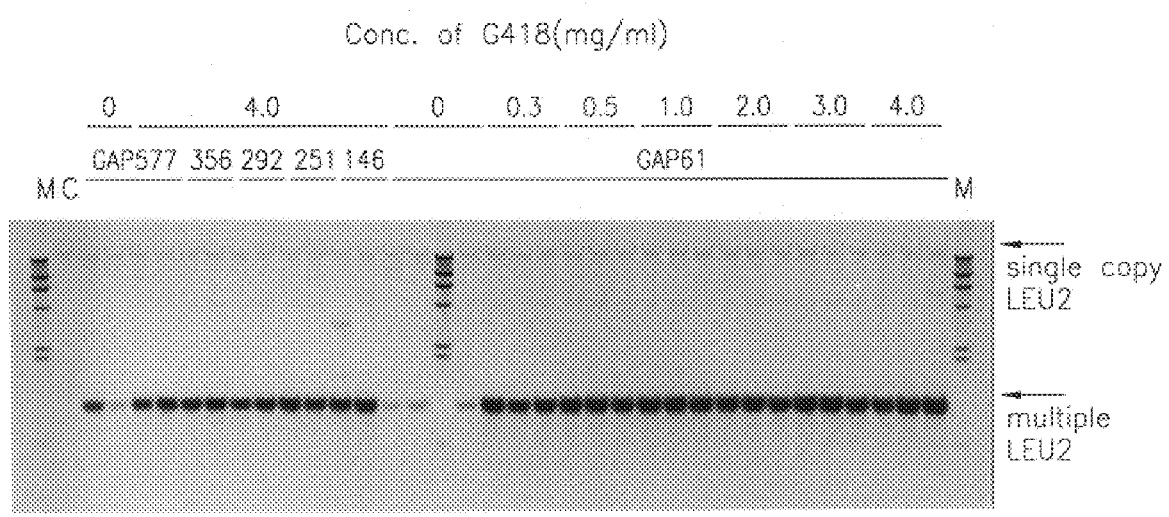

The result is shown in FIG. 11C, wherein the single leu2 gene derived from the host itself appears at 30.0 kb position and the multiple leu2 genes originating from the plasmid are shown at about 1.0 kb position. Further, the transformants containing plasmid pGLG61 showed a signal stronger than those of other transformants at 4 mg/ml of G418, and its signal became stronger as the concentration of G418 increased.

For the purpose of determining the copy number of the integrated gene as function of the concentration of G418, the genomic DNAs of transformants containing pGLG61 in FIG. 11C were 25-fold diluted with TE buffer, and subjected to Southern blotting analysis by employing the same probe as used in FIG. 11C. The integration copy number was determined in accordance with the procedure of Example 10.

The result is shown in Table 10.

TABLE 10

| Conc. of G418 (mg/ml) | 0 | 0.3 | 0.5 | 1.0 | 2.0 | 3.0 | 4.0 |
|---|---|---|---|---|---|---|---|
| Copy number | 1.0 | 10.8 | 16.1 | 22.1 | 23.9 | 35.3 | 46.9 |

The copy number of introduced genes increased with the concentration of G418 and reached a maximum of 50 at 4 mg/ml of G418.

Based on the above result, it is possible to regulate the copy number of introduced genes from 1 to 50 copies by way of adjusting the concentration of G418.

EXAMPLE 14
Properties of plasmids containing HARS36, TEL135 and TEL61

Plasmid pGLG61 prepared in Example 12 was digested with PstI and SalI to cut out TEL188, and in the place of TEL188, HARS36, TEL61 or TEL135 was inserted to the plasmid instead of TEL188 to construct a plasmid having HARS36, TEL61 or TEL135. H. polymorpha DL-1L(leu2) cells were transformed by the resulting plasmid and the copy number of the introduced genes was determined in accordance with the procedure of Example 10.

The result is shown in Table 11.

TABLE 11

| ARS | Conc. of G418 (mg/ml) | | | | | | |
|---|---|---|---|---|---|---|---|
| | 0 | 0.3 | 0.5 | 1.0 | 2.0 | 3.0 | 4.0 |
| HARS36 | 1.0 | 8.4 | 14.3 | 19.4 | 21.0 | 32.1 | 42.3 |
| TEL61 | 1.0 | 9.2 | 13.1 | 19.9 | 22.7 | 37.3 | 49.0 |
| TEL135 | 1.0 | 6.5 | 11.3 | 17.4 | 18.6 | 29.9 | 41.2 |

In each case of the transformants containing HARS36, TEL61 and TEL135, the copy number of introduced gene increases as the concentration of G418 increases, as in the case of TEL188.

EXAMPLE 15
Production of EGF by using the ARS of H. polymorpha
(Step 1) Construction of expression vector For the purpose of producing human epidermal growth factor(hEGF) in H. polymorpha, plasmid pUREGF containing HARS36 and hEGF gene was constructed in accordance with the procedure of FIG. 13, as follows.

Plasmid pAA3 (Tajima et al., Mol. Cell. Biol., 6, 246–256 (1986)) was digested with HindIII to obtain 1.2 kb DNA fragment comprising URA3 gene originating from S. cerevisiae. Plasmid pCE36 obtained in (Step 4 ) of Example 1 was digested with HindIII, and the 1.2 kb DNA fragment obtained above was inserted to said digested plasmid to construct plasmid pCEU36. Plasmids pCEU36 and pA-EGF3 (Yong-Ik Oh, Kor. J. Appl., Microbiol. Biotechnol., 22, 477(1994)) were digested separately with EcoRI, and then the digestion products were ligated with each other to construct plasmid pCEU-EGF. This plasmid was digested with SalI and NotI to cut out leucine gene of *H. polymorpha*(HLEU2) and thereby constructing plasmid pUREGF comprising URA3 gene, HARS36 and hEGF.

*E. coli* DH5α carrying plasmid PUREGF (*E. coli* DH5α/pUREGF) was deposited on Jan. 14, 1997 with the Korean Collection for Type Cultures (KCTC) (Address: KCTC, KRIBB, #52, Oun-dong, Yusong-ku, Taejon, 305-333, Republic of Korea) under the accession number of KCTC 8771P.

(Step 2) Preparation of uracil-auxotrophic *H. polymorpha*

As a host cell for the production of EGF, a uracil-auxotrophic *H. polymorpha* cell was prepared as follows.

*H. polymorpha* DL-1L(leu2) cells were irradiated with UV light to induce mutation, and $5 \times 10^4$ cells of survived mutants were cultured on a minimal medium containing 20 μg/ml of uracil and 70 μMg/ml of 5-fluoroorotic acid (5-FOA) to select resistant colonies. 1,000 resistant colonies selected therefrom were transferred to a minimal medium without uracil by replica plating and 22 uracil-auxotrophs were selected therefrom. A strain named *H. polymorpha* DLU10, which has a relatively high growth rate, was selected and used as a host cell for the production of hEGF.

(Step 3) Quantification of hEGF produced

*H. polymorpha* DLU10 cells were transformed with plasmid pUREGF and selected on minimal medium (0.67% yeast nitrogen base without amino acid, 2% glucose, 2% agar) at 37° C. for 72 hours. *H. polymorpha* DLU10 carrying plasmid pUREGF (*H. polymorpha* DLU10/pUREGF) was deposited on Jul. 24, 1997 with the Korean Collection for Type Cultures (KCTC) (Address: KCTC, KRIBB, #52, Oun-dong, Yusong-ku, Taejon, 305-333, Republic of Korea) under the terms of the Budapest Treaty on the International Recognition of the Deposit of Microorganism for the Purpose of Patent Procedure under the accession number of KCTC 0356BP.

The transformants were stabilized as mentioned in Example 7 and then cultured on the YPD medium at 37° C. for 24 hours. The colonies grown on the YPD medium were transferred to a nitrocellulose membrane, the membrane was transferred to an inducing medium (10 g yeast extract, 20 g peptone, 20 ml methanol, 20 g bactoagar per 1 l of distilled water) and then cultured at 37° C. for 24 hours. The nitrocellulose membrane was washed with a washing solution (500 mM NaCl in 20 mM Tris-HCl, pH 7.5) and treated with 0.4% glutaraldehyde at room temperature for 45 min. to immobilize the secreted hEGF. The membrane was washed twice with TBST (TBS: 10 mM Tris, 0.15 mM NaCl, pH 7.4, 0.05% Tween 20) each for 5 min., treated with 5% non-fat dried milk (w/v in TBS) at room temperature for 1 hour and, then, washed twice with TBST each for 5 min.

The membrane was treated with a dilution comprising monoclonal antibodies against hEGF (#05-109, UBI, U.S.A.) in 10,000-fold volume of TBS at room temperature for 1 hour, washed twice with TBST each for 5 min. The membrane was treated with a dilution containing a second antibody, i.e., alkaline phosphatase conjugated goat anti-mouse IgG (Bio-Rad) in 3,000-fold volume of TBS at room temperature for 1 hour, washed three times each for 5 min. with TBST and TBS, respectively.

A substrate solution for alkaline phosphatase was prepared by diluting 5% NBT(nitro blue tetrazolium) and 5% BCIP(bromochloroindolyl phosphate) in alkaline phosphatase reaction buffer (100 mM Tris, pH 9.5), 100 mM NaCl, 15 mM $MgCl_2$) to 0.33% NBT and 0.165% BCIP, and then added to the membrane for color development. The violet signals were observed at the positions of the colonies where hEGF has been expressed. Some transformants showing strong color intensity were selected since the color intensity is proportional to the amount of secreted hEGF.

The selected transformants were inoculated in YP-glycerol medium (1% yeast extract, 2% peptone and 2% glycerol) and cultured with shaking at 37° C. for 24 hours. The cultured cells were inoculated to a concentration of 1% in YP medium(1% yeast extract and 2% peptone) containing 2% methanol and then cultured with shaking at 37° C. Culture samples were collected every 12 hours and the amount of secreted hEGF in each sample was determined by enzyme-linked immunosorbent assay(ELISA) as follows.

Each sample was centrifuged at 5,000×g for 5 min. to obtain a supernatant, which was then diluted with 50,000-fold volume of antigen coating buffer (0.1M sodium carbonate buffer, pH 9.6). The dilutions were added to the wells of a microtiter plate (Nunc-immunomodule) in an amount of 100 μl/well and incubated at 37° C. for 2 hours.

The wells were washed once with PBST (phosphate buffered saline(PBS)+0.1% Tween 20), PBS containing 0.05% (w/v) gelatin was added to the wells in an amount of 100 μl/well, and the plate was incubated at 37° C. for 1 hour. The wells were washed with PBST and 100 μl of a dilution comprising monoclonal antibodies against hEGF (#05-109, UBI, U.S.A.) in 10,000-fold volume of PBS containing 0.05% gelatin was added to every well.

The wells were reacted at 37° C. for 2 hours, washed once with PBST, and a solution comprising horseradish peroxidase(HRP) conjugated goat anti-mouse IgG (Bio-Rad Company, Richmond, Calif. 94804, U.S.A, 0.1 mg protein/ml) which was diluted with 3,000-fold volume of PBS containing 0.05% gelatin was added to the wells in an amount of 100 μl/well.

The resultant was incubated at 37° C. for 1 hour and washed 3 times with PBST. Thereafter, color development was carried out by using TMB substrate kit (Pierce, U.S.A.). 100 μl of a substrate solution, prepared by mixing a 0.04% TMB (3,3', 5,5'-tetramethylbenzidine) solution and a 0.02% hydrogen peroxide solution in a citrate buffer in a ratio of 1:1, was added to each well and, after 15 min., the reaction was quenched by adding 100 μl of 2M sulfuric acid to each well. Quantification of hEGF was carried out by determining O.D. of each well at 450 nm by employing 96-well plate autoreader (THERMOmax, Molecular Devices, U.S.A.). Standard hEGF sample (UBI, #01-107) was employed at dilutions range from 0.25 ng/well to 5 ng/well. *H. polymorpha* UR2 selected by the above procedure is particularly effective in producing hEGF, showing a productivity of 474.96 mg hEGF/L, which is higher by a factor of 20 than that (24.0 mg/L) of the control strain *H. polymorpha* 2–21 containing HARS3 originated from CBS4732 strain (Yong-Ik Oh, supra).

(Step 4) Determination of the integration patterns of introduced hEGF genes

Figure 14A:
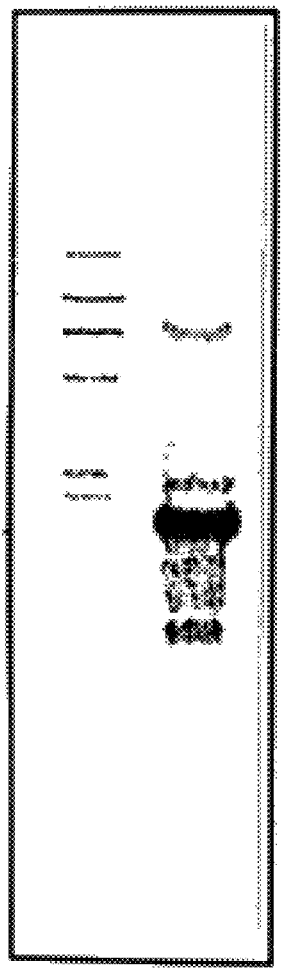
FIGS. 14A and 14B represent the results of Southern blotting analyses confirming the form and position of hEGF gene inserted in the chromosome of *Hansenula polymorpha* UR2, respectively.

For the purpose of determining the copy number of hEGF genes introduced to *H. polymorpha,* the entire chromosome of *H. polymorpha* UR2 was isolated, digested with EcoRV and StuI and, then, subjected to Southern blotting analysis by employing MOX promoter gene as a probe. The result is shown in FIG. 14A, wherein the signal of the single copy of MOX promoter which originated from *H. polymorpha* UR2 itself appears at 0.8 kb position and the signal of the foreign MOX promoter introduced for the production of hEGF manifests itself at 1.8 kb position. Comparison of these two signals reveals that the signal of the introduced foreign MOX promoter is much stronger than that of the original MOX promoter, which suggests that multiple copies of the foreign MOX promoter were introduced to the chromosome of *H. polymorpha* UR2.

Figure 14B:
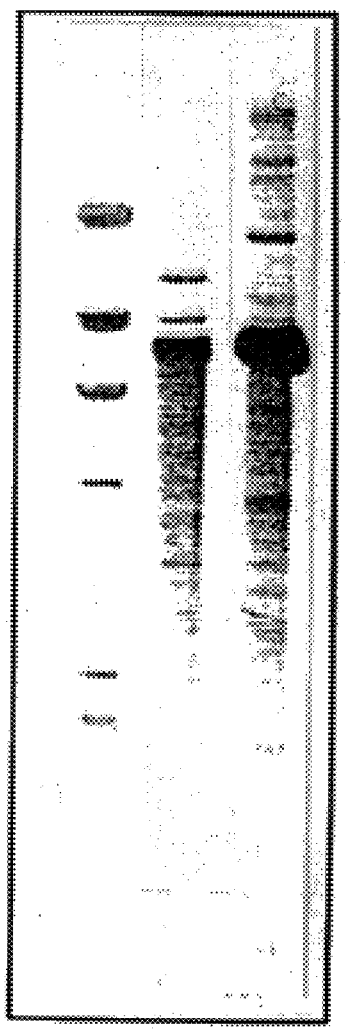

For the purpose of examining whether the foreign gene was introduced in tandem repeat units, plasmid pUREGF which has only one BamHI site and the chromosome of *H. polymorpha* UR2 were respectively cut with BamHI, and subjected to Southern blotting analysis by employing URA3 gene of *S. cerevisiae* as a probe. The result is shown in FIG. 14B, wherein the chromosome of UR2 showed a strong signal at a position corresponding to plasmid PUREGF and a single weak signal which corresponds to a flanking fragment of the plasmid and the chromosome. The other flanking fragment was not observed because it does not have a homology with the probe. Accordingly, it was confirmed that hEGF gene was introduced to the chromosome of *H. polymorpha* UR2 in multiple tandem repeats.

While the invention has been described with respect to the above specific embodiments, it should be recognized that various modifications and changes which may be apparent to those skilled in the art to which the invention pertains may be made and also fall within the scope of the invention as defined by the claims that follow.

What is claimed is:

1. An autonomously replicating sequence isolated from *Hansenula polymorpha* DL-1(KCTC 0512BP), which has a repeating unit of 5'-GGGTGGCG-3' at its 3'-end.

2. The autonomously replicating sequence of claim 1 which has the nucleotide sequence of SEQ ID NO: 1, 2, 3 or 4.

3. A polynucleotide encoding glyceraldehyde-3-phosphate dehydrogenase of *Hansenula polymorpha*, which has the nucleotide sequence of SEQ ID NO: 5.

4. A promoter of glyceraldehyde-3-phosphate dehydrogenase gene of *Hansenula polymorpha*, which has the nucleotide sequence of SEQ ID NO: 7.

5. A fragment of glyceraldehyde-3-phosphate dehydrogenase promoter of *Hansenula polymorpha*, which has a nucleotide sequence selected from the group consisting of the 219th–796th, 441st–796th, 505th–796th, 546th–796th, 651st–796th and 736th–796th nucleotides of SEQ ID NO: 7.

6. An expression vector for multiple tandem integration of a polynucleotide encoding a foreign protein into the chromosome of *Hansenula polymorpha*, which comprises: an autonomously replicating sequence(ARS) isolated from *Hansenula polymorpha* DL-1(KCTC 0512BP), which has a repeating unit of 5'-GGGTGGCG-40 at its 3'-end; a promoter; a polynucleotide encoding a foreign protein, which is located in the downstream of said promoter; and a terminator which is located in the downstream of said polynucleotide, wherein the ARS, the promoter, the polynucleotide and the terminator are operatively linked so as to form an expression cassette.

7. The expression vector of claim 6, wherein the autonomously replicating sequence has the nucleotide sequence of SEQ ID NO: 1, 2, 3 or 4.

8. The expression vector of claim 6, wherein the promoter is GAPDH promoter isolated from *Hansenula polymorpha* DL-1(KCTC 0512BP) or a fragment thereof selected from the group consisting of: the 219th–796th, 441st–796th, 505th–796th, 546th–796th, 651st–796th and 736th–796th nucleotides of SEQ ID NO: 7.

9. The expression vector of claim 7, which is plasmid pUREGF.

10. The expression vector of claim 9, wherein the GAPDH promoter has the nucleotide sequence of SEQ ID NO: 7.

11. The vector of claim 8, wherein the foreign protein is selected from the group consisting of: hirudin, human epidermal growth factor (hEGF), human serum albumin(HSA), prourokinase, urokinase, human $\alpha_1$-antitrypsin, hepatitis B surface antigen(HBsAg), lipocortins, interferons, lysozyme, interleukins, colony stimulating factors, tissue plasminogen activators, insulin, factor VIII, superoxide dismutase, calcitonin, insulin-like growth factors and growth hormones.

12. The vector of claim 8, wherein the polynucleotide encoding a foreign protein is a fused polynucleotide wherein the polynucleotide encoding the foreign protein is fused with the GAPDH gene or a fragment thereof isolated from *Hansenula polymorpha* DL-1(KCTC 0512BP).

13. A *Hansenula polymorpha* cell transformed with the expression vector of claim 6 or 8.

14. The *Hansenula polymorpha* cell of claim 13, which is *Hansenula polymorpha* DLU10(leu2, ura3)/pUREGF (KCTC 0356BP).

15. The *Hansenula polymorpha* cell of claim 13, which is *Hansenula polymorpha* DL-1L(leu2)/pHGAP-HIR(KCTC 0357BP).

16. A process for the production of a foreign protein in *Hansenula polymorpha* comprising the steps of:

(a) transforming *Hansenula polymorpha* cells with the expression vector of claim 6 or 8;

(b) culturing the transformed *Hansenula polymorpha* cells in a suitable medium to produce the foreign protein; and (c) recovering the foreign protein from the culture.

17. The expression vector of claim 10, which is plasmid pHGAP-HIR.

18. The process of claim 16, wherein the foreign protein is selected from the group consisting of: hirudin, human epidermal growth factor(hEGF), human serum albumin (HSA), prourokinase, urokinase, human $\alpha_1$-antitrypsin, hepatitis B surface antigen(HBsAg), lipocortins, interferons, lysozyme, interleukins, colony stimulating factors, tissue plasminogen activators, insulin, factor VIII, superoxide dismutase, calcitonin, insulin-like growth factors and growth hormones.

19. An expression vector for multiple tandem integration of a polynucleotide encoding a foreign protein into the chromosome of *Hansenula polymorpha*, which comprises a selection cassette containing an autonomously replicating sequence(ARS) isolated from *Hansenula polymorpha* DL-1 (KCTC 0512BP), which has a repeating unit of 5'-GGGTGGCG-3' at its 3'-end, a first promoter, a dominant selection marker located in the downstream of said first promoter, and an auxotrophic marker, wherein the ARS, the promoter and the marker are operatively linked so as to form a cassette; and an expression cassette containing a second promoter, a polynucleotide encoding a foreign protein, which is located in the downstream of said second promoter, and a terminator which is located in the downstream of said polynucleotide, wherein the promoter, the polynucleotide, and the terminator are operatively linked so as to form a cassette.

20. The expression vector of claim 19, wherein the autonomously replicating sequence has the nucleotide sequence of SEQ ID NO: 1, 2, 3 or 4.

21. The expression vector of claim 19, wherein at least one of the first and the second promoters is GAPDH promoter isolated from *Hansenula polymorpha* DL-1 (KCTC 0512BP) or a fragment thereof selected from the group consisting of: the 219th–796th, 441st–796th, 505th–796th, 546th–796th, 651st–796th and 736th–796th nucleotides of SEQ ID NO: 7.

22. The expression vector of claim 19, wherein the auxotrophic marker is LEU2 or URA3 gene of a yeast.

23. The expression vector of claim 19, wherein the dominant selection marker is aminoglycoside-3-phosphate transferase(APH) gene isolated from *E. coli* transposon Tn903.

24. A method for the selection of *Hansenula polymorpha* transformant having multiple copies of an integrated foreign gene, which comprises the steps of:

(a) transforming *Hansenula polymorpha* with the vector of claim 19;

(b) culturing the transformed *Hansenula polymorpha* on a minimal medium to select transformants;

(c) culturing the selected transformants alternately on a composite medium and on a minimal medium to stabilize the transformants;

(d) culturing the stabilized transformants on a medium containing an antibiotic; and (e) selecting transformants resistant to the antibiotic as the transformants having multiple copies of the integrated foreign gene.

25. The expression vector of claim 21, wherein the GAPDH promoter has the nucleotide sequence of SEQ ID NO: 7.

26. The method of claim 24, wherein the autonomously replicating sequence in the vector has the nucleotide sequence of SEQ ID NO: 1, 2, 3 or 4.

27. The method of claim 24, wherein the first promoter in the vector is GAPDH promoter isolated from *Hansenula polymorpha* DL-1(KCTC 0512BP) or a fragment thereof selected from the group consisting of: the 219th–796th, 441st–796th, 505th–796th, 546th–796th, 651st–796th and 736th–796th nucleotides of SEQ ID NO: 7.

28. The method of claim 24, wherein the auxotrophic marker in the vector is LEU2 or URA3 gene of a yeast.

29. The method of claim 24, wherein the dominant selection marker in the vector is aminoglycoside-3-phosphate transferase(APH) gene isolated from *E. coli* transposon Tn903 and the antibiotic is G418.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 1227 base pairs
      (B) TYPE: nucleic acid
      (C) STRANDEDNESS: single
      (D) TOPOLOGY: linear (ii) MOLECULE TYPE: genomic DNA (ix) FEATURE:
      (D) OTHER INFORMATION: autonomously replicating sequnce of
         Hansenula polymorpha DL-1(ATCC 26012)

(xi) SEQUENCE DESCRIPTION: SEQ ID NO: 1:

```
GATCGAAGTA CCCTGGGGGT AGTATCTACT GCGCCACAAA GTCTGCCGTG           50

CGGATTCACC CAAGCAATTC GGAAGGAGCT GATCAGCACT AGGATCCGTG          100

TGATGGAGAT TGACCCTGGT GCTGTGGAGA CGGAGTTCTC GCTGGTGCGG          150

TTTGGCGGCG ATGCACAAAA GCCAGCAAGG TGTACGAAGG CTACGAGCCG          200

CTGAGTGCGA AGGACATTTC AGACGTGGTT GTGTTCAACT GCAGTCGGCG          250

GGCCAACGTG GTTGTGGCGG AGTCGGTGGT GTTTCCAACT GCGCAGGCGG          300

GAAGCTACCA TAGACATAGG AGTGAGCCAA GGGAGGGAAC AGAGAAGAAT          350

TAGAGAGGGA ATTAGAGAGG AATTAGAGCA AGTAGAGCTA TAGAAGAGAT          400

AAGCTAAGTC AAGAATTAGA GCAAGTAGGG GCAAGTTTAA TATATGTGGA          450

TTAATAAAGG TGAGAAATTA GATGGGAGGA GCGGCAGGAA ACGGTGTAGG          500

GATGCGGTGA GGGGAGCGGA CGCGGTTGGT TTTAGGATGC GGTCTGAGGG          550

TGGCGGGGTG GCGGGGTGGC GGGGTGGTGG GGTGGCGGGG TGGCGGGGTG          600

GCGGGGTGGC GGGGTGGCGG GGTGGCGGGG TGGCGGGGTG GCGGGGTGGC          650

GGGGTGGCGG GGTGGCGGGG TGGCGGGGTG GCGGGGTGGC GTGATCATCG          700

GGTACAACAT TGCCAACTTT GACTTCCCGT ACCTGATCAA CAGGGCTCGG          750

GCGCTCGGCG TCCACGACTT CCCGTACTTC TCGCGTCTGA AGAATAGCAA          800

GCAGGAGATC AAGGACACAT TTTTCAGCTC GCGCGCGTAC GGCAGCCGCG          850

AAAACAAGGT GGTCAATATT GAGGGCCGCA TGCAGCTGGA CCTGCTCCAA          900

TTCATCCAGC GCGAGTACAA ACTGCGCTCG TACACGCTGA ACGCGGTGTC          950

GGCACATTTT CTTAACGAAC AGAAAGAGGA TGTGCAGCAC TCGATCATCA         1000

CAGATCTCCA GAACGGCAAC CAGGAGACCA GAAGGCGGCT GGCAGTGTAC         1050

TGTCTGAAAG ACGCGTACTT GCCGTTGCGA CTAGCCGAAA AACTCATGTG         1100
```

```
TCTGGTCAAC TACACAGAGA TGGCCAGGGT GACCGGCGTG CCGTTCAGTT         1150

TCCTCCTCTC GCGTGGCCAG CAGATTAAGG TCATCTCGCA GCTGTTCCGC         1200

AAGTGTCTGG ACCTGGACAT TGTGATC                                  1227

(2) INFORMATION FOR SEQ ID NO: 2:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: genomic DNA (ix) FEATURE:
        (D) OTHER INFORMATION: autonomously replicating sequnce of
            Hansenula polymorpha DL-1(ATCC 26012)

(xi) SEQUENCE DESCRIPTION: SEQ ID NO: 2:

CTGCAGTCGG CGGGCCAACG TGGTTGTGGC GGAGTCGGTG GTGTTTCCAA           50

CTGCGCAGGC GGGAAGCTAC CATAGACATA GGAGTGAGCC AAGGGAGGGA          100

ACAGAGAAGA ATTAGCGAGG GAATTAGAGA GGAATTAGAG CAAGTAGAGC          150

TATAGAAGAG ATAAGCTAAG TCAAGAATTA GAGCAAGTAG GGGCAAGTTT          200

AATATATGTG GATTAATAAA GGTGAGAAAT TAGATGGGAG GAGCGGCAGG          250

AAACGGTGTA GGGATGCGGT GAGGGGAGCG GACGCGGTTG GTTTTAGGAT          300

GCGGTCTGAG GGTGGCGGGG TGGCGGGGTG GCGGGGTGGT GGGGTGGCGG          350

GGTGGCGGGG TGGCGGGGTG GCGGGGTGGC GGGGTGGCGG GGTGGCGGGG          400

TGGCGGGGTG GCGGGGTGGC GGGGTGGCGG GGTGGCGGGG TGGCGGGGTG          450

GCG                                                            453

(2) INFORMATION FOR SEQ ID NO: 3:

(i) SEQUENCE CHARACTERISTICS:
        (A) LENGTH: 405 base pairs
        (B) TYPE: nucleic acid
        (C) STRANDEDNESS: single
        (D) TOPOLOGY: linear (ii) MOLECULE TYPE: genomic DNA (ix) FEATURE:
        (D) OTHER INFORMATION: autonomously replicating sequnce of
            Hansenula polymorpha DL-1(ATCC 26012)

(xi) SEQUENCE DESCRIPTION: SEQ ID NO: 3:

CTGCAGTCGA CAGGCCAACG TGGTTGTGGC GGAGTCGGTG GTGTTTAGAG           50

AGGAATTAGA GCAAGTAGAA GTATAGAAGG AATAAGCCAA GTAGAGACAA          100

GTTTAATATA TGTAGATTAA TAAAGGTGAG GAATTAGATG GGGAGGAAGC          150

GGCAGGAAGC GGTGTAGGGA TGCGGCGAGG AAAGCAGAGG CAGCTGGTTT          200

CAGGACGCGG TCTGAGGCCT GGGGTGGCGG GGTGGCGGGG TGGCGGGGTG          250

GCGGGGTGGC GGGGTGGCGG GGTGGCGGGG TGGCGGGGTG GCGGGGTGGC          300

GGGGTGGCGG GGTGGCGGGG TGGCGGGGTG GCGGGGTGGC GGGGTGGCGG          350

GGTGGCGGGG TGGCGGGGTG GCGGGGTGGC GGGGTGGCGG GGTGGCGGGG          400

TGGCG                                                          405
```

(2) INFORMATION FOR SEQ ID NO: 4:

(i) SEQUENCE CHARACTERISTICS:
        (A) LENGTH: 460 base pairs
        (B) TYPE: nucleic acid
        (C) STRANDEDNESS: single
        (D) TOPOLOGY: linear (ii) MOLECULE TYPE: genomic DNA (ix) FEATURE:
        (D) OTHER INFORMATION: autonomously replicating sequnce of
            Hansenula polymorpha DL-1(ATCC 26012)

(xi) SEQUENCE DESCRIPTION: SEQ ID NO: 4:

```
CTGCAGTCGG CGGGCCAACG TGGTTGTGGC GGAGTCGGTG GTGTTTCCAA        50

GTGCGCAGGC GGGAAGCTAC CATAGACATA GGAGTGAGCC AAGGGAGGGA       100

ACAGAGAGGA ATTAGAGAGG GAATTAGAGA AGAATCAGAG CAAGTAGAGC       150

TATAGAAGGA ATAAGCCAAG TTAAGAATTA GAGCAAGTAG AGGCAAGTTT       200

AATATATGTA GATTAATAAA GGTGAGAAAT TAGATGGGGA GGAAGCGGCA       250

GGAAGCGGTG TAGGGATGCG GTGAGAAGAG CGGCCGAGCT GGTTTGAGGA       300

TGCGGTCTGA GGATTGGGGT GGCGGGGTGG CGGGGTGGCG GGGTGGCGGG       350

GTGGCGGGGT GGCGGGGTGG CGGGGTGGCG GGGTGGCGGG GTGGCGGGGT       400

GGCGGGGTGG CGGGGTGGCG GGGTGGCGGG GTGGCGGGGT GGCGGGGTGG       450

CGGGGTGGCG                                                  460
```

(2) INFORMATION FOR SEQ ID NO: 5:

(i) SEQUENCE CHARACTERISTICS:
        (A) LENGTH: 2375 base pairs
        (B) TYPE: nucleic acid
        (C) STRANDEDNESS: single
        (D) TOPOLOGY: linear (ii) MOLECULE TYPE: genomic DNA (ix) FEATURE:
        (D) OTHER INFORMATION: glyceraldehyde-3-phosphate
            dehydrogenase gene of Hansenula
            polymorpha DL-1(ATCC 26012)

(xi) SEQUENCE DESCRIPTION: SEQ ID NO: 5:

```
CCTTTGCTCA ATGCCGTTTT GGTGATATCG ACCAATTGCT GGTTAACGGT        50

GTCGTTGCCG TACTTGTAAT AATAAGTACC GCAGCCAAAG GCTAATCTTG       100

GAATGCCCGA GGAGGTGGTT GGAATGCTCA TTTCGAATAC AGTCAACAAT       150

CAATTGAGTT TGTATTTATA GCCAATTGGT CATTAATAAT CAGGCTTCCT       200

GCATGGTTTA GAGGTTGGTC TAGACTACAT CCGTGCACCA GAAAAGAGGC       250

GGGCCACGGA GGAAAAGGTG ACAACTCGCA AAGTTGCAAC AACTGCTATG       300

GCTCCAGCAC GGTGCGTGGG GTAAAGACAA TCTCCGGGAA CCGGTCCCGA       350

AACCGAGAAA GAGGGTTTTA AGCCTGTGTC CTCTGCGGAG GTGGTGTAGC       400

ACTTCTTATT GTCCTTTGGG CCGCTCCGGC GGTAGAGCTT CCATGGAACA       450

ACCTTGCACG GACAGGCAAG TCCCCGAGAC GCCTTGTTGG GTGATGTCCA       500

CTTCTGGCTA TACAGAGCTT TATATCACCT TACTGAACGC TAGAGTAGAC       550

CCAATTCCCG GCTCACACCA CCCTTACATG CAGAGCTAAC CAATAAGGTA       600

ATTAATTAAC ACTATATAGC TCGTGGTGAA CACTGGCCCG GAGTAGTCAT       650
```

```
ACGTGTAGGT TTTTGGCGTG ATGAAAATCA GGTGGCGCAC GACTTTTCGT         700

AAAGTTCGGG AGGGAGTGCT GCAAACGGCA TATAAGGACC AGTTTTTCTC         750

GCACATTATC AATTGCTCTT TAGTACAAAG ATAATATAGA AACAATATGA         800

CCGCAAACGT TGGAATTAAT GGATTTGGAA GAATTGGTAG ACTGGTGTTG         850

AGAATTGCCT TGAGCAGAGA CGACATCAAC GTCATTGCTA TCAATGATCC         900

ATTCATTGCT CCTGATTACG CCGCTTACAT GTTCAAGTAC GACTCTACCC         950

ACGGAAAGTT CAAGGGAACT GTCACCCACG AGGGCAAGTA CTTGGTCATT        1000

AACGGCAAGA AGATTGAGGT CTTCCAAGAG AGAGACCCAG CAAACATCCC        1050

ATGGGGTAAG GAGGGCGTCG ACTACGTTCT TGACTCCACT GGAGTTTTCA        1100

CCACCATCGA GGGTGCTCAA AAGCACATTG ATGCTGGTGC CAAGAAGGTC        1150

ATCATCACTG CTCCATCTAA GGACGCTCCA ATGTTCGTCG TCGGTGTGAA        1200

CCACGAGGAG TACACTCCAG ACATCAAGAT CCTGTCTAAC GCTTCTTGTA        1250

CCACCATCTG TCTGGTTCCA CTGGCCAAGG TTATCACTGA CATCTTCGGA        1300

ATCGAGGAAG GTTTGATGAC CACCGTCCAC TCCATCACCG CTACTCAAAA        1350

GACTGTCGAC GGTCCATCCC ACAAGGACTG GAGAGGTGGT AGAACTGCTT        1400

CTGGTAACAT CATCCCATCC TCCACCGGTG CTGCCAAGGC TGTCGGAAAG        1450

GTCCTTCCAG CATTGGCCGG TAAGCTCACT GGTATGTCCA TGAGAGTCCC        1500

AACCACTGAT GTTTCTGTTG TTGACTTGAC CGTCAACCTT AAGAAGCCAA        1550

CCACCTACGA GGACATTTGT GCCACCATGA AGAAGGCTGC TGAGGGCCCA        1600

TTGGCTGGAA TTCTTGGATA CACCGACGAG GCTGTTGTTT CGTCTGACTT        1650

CTTGACCGAC AGCAGATCCT CTGTCTTTGA CGCCAAGGCC GGTATCTTGT        1700

TGACCCCAAC CTTCGTCAAG CTCGTTTCCT GGTACGACAA TGAGTACGGT        1750

TACTCTACCA GAGTTGTTGA CTTGCTTCAG CACGTTGCTA AGGTTTCCGC        1800

CTAAGCACGG CCTCATCTAC ATATTTACGG CTTAACTGAT TTTTATAGTT        1850

AAGGAGAAAA AAAGTTCAAC ATACGTCATT ATTATTGTAC GCGCTTTCGT        1900

GTTTCAAACT TGGCTGCCAT GATAAATAAA TCTATTGTTG CTTGCTATGT        1950

AAAAATTATT TGATTACTTC TTCCATGCAC TTTCTTTATT TGGATTGTGG        2000

TCCTGGTGGC ATTGGGGACT CTCTGGCATT ATACCCGTAT CCTGATACGG        2050

AACCGTTCTA AATATATTTC GCGACAATTC AGGAGCCGCA CGCTGCTTCT        2100

AGCGCATCAT GAGATCCACG TCATGCATGG TTGTAGACAA GGACAAGGGG        2150

CAGTAGCTCA GAAGGGCGTC GTGTTCTGGA CCGCATATGG ATACAATCAA        2200

TATCGGCATT GTTTTCGGTA CTGGGCACCT GCTTGCTGCT CAATCACCTC        2250

TTGTCGCTCC CCGCTCCAAT CTGATTTTCG CGTGAATAGG GCAAAAAAAA        2300

ATTCTCTGCC GGCTTGGGGC TGATCGGTGC ATTGAAATTT CCTTATACGT        2350

GTTCCAGGTT TCAATTTACT CTAGA                                  2375
```

(2) INFORMATION FOR SEQ ID NO: 6:

(i) SEQUENCE CHARACTERISTICS:
      (A) LENGTH: 335 amino acids
      (B) TYPE: amino acid
      (D) TOPOLOGY: linear (ii) MOLECULE TYPE: protein (ix) FEATURE:
  (D) OTHER INFORMATION: glyceraldehyde-3-phosphate
      dehydrogenase of Hansenula polymorpha
      DL-1(ATCC 26012)

(xi) SEQUENCE DESCRIPTION: SEQ ID NO: 6:

```
Met Thr Ala Asn Val Gly Ile Asn Gly Phe Gly Arg Ile Gly Arg
 1               5                  10                  15

Leu Val Leu Arg Ile Ala Leu Ser Arg Asp Asp Ile Asn Val Ile
             20                  25                  30

Ala Ile Asn Asp Pro Phe Ile Ala Pro Asp Tyr Ala Ala Tyr Met
             35                  40                  45

Phe Lys Tyr Asp Ser Thr His Gly Lys Phe Lys Gly Thr Val Thr
             50                  55                  60

His Glu Gly Lys Tyr Leu Val Ile Asn Gly Lys Lys Ile Glu Val
             65                  70                  75

Phe Gln Glu Arg Asp Pro Ala Asn Ile Pro Trp Gly Lys Glu Gly
             80                  85                  90

Val Asp Tyr Val Leu Asp Ser Thr Gly Val Phe Thr Thr Ile Glu
             95                 100                 105

Gly Ala Gln Lys His Ile Asp Ala Gly Ala Lys Lys Val Ile Ile
            110                 115                 120

Thr Ala Pro Ser Lys Asp Ala Pro Met Phe Val Val Gly Val Asn
            125                 130                 135

His Glu Glu Tyr Thr Pro Asp Ile Lys Ile Leu Ser Asn Ala Ser
            140                 145                 150

Cys Thr Thr Asn Cys Leu Ala Pro Leu Ala Lys Val Ile Asn Asp
            155                 160                 165

Ile Phe Gly Ile Glu Glu Gly Leu Met Thr Thr Val His Ser Ile
            170                 175                 180

Thr Ala Thr Gln Lys Thr Val Asp Gly Pro Ser His Lys Asp Trp
            185                 190                 195

Arg Gly Gly Arg Thr Ala Ser Gly Asn Ile Ile Pro Ser Ser Thr
            200                 205                 210

Gly Ala Ala Lys Ala Val Gly Lys Val Leu Pro Ala Leu Ala Gly
            215                 220                 225

Lys Leu Thr Gly Met Ser Met Arg Val Pro Thr Thr Asp Val Ser
            230                 235                 240

Val Val Asp Leu Thr Val Asn Leu Lys Lys Pro Thr Thr Tyr Glu
            245                 250                 255

Asp Ile Cys Ala Thr Met Lys Lys Ala Ala Glu Gly Pro Leu Ala
            260                 265                 270

Gly Ile Leu Gly Tyr Thr Asp Glu Ala Val Val Ser Ser Asp Phe
            275                 280                 285

Leu Thr Asp Ser Arg Ser Ser Val Phe Asp Ala Lys Ala Gly Ile
            290                 295                 300

Leu Leu Thr Pro Thr Phe Val Lys Leu Val Ser Trp Tyr Asp Asn
            305                 310                 315

Glu Tyr Gly Tyr Ser Thr Arg Val Val Asp Leu Leu Gln His Val
            320                 325                 330

Ala Lys Val Ser Ala
            335
```

(2) INFORMATION FOR SEQ ID NO: 7:

(i) SEQUENCE CHARACTERISTICS:

(A) LENGTH: 796 base pairs
        (B) TYPE: nucleic acid
        (C) STRANDEDNESS: single
        (D) TOPOLOGY: linear (ii) MOLECULE TYPE: genomic DNA (ix) FEATURE:
        (D) OTHER INFORMATION: glyceraldehyde-3-phosphate
            dehydrogenase promoter of
            Hansenula polymorpha DL-1
        (ATCC 26012)

(xi) SEQUENCE DESCRIPTION: SEQ ID NO: 7:

```
CCTTTGCTCA ATGCCGTTTT GGTGATATCG ACCAATTGCT GGTTAACGGT              50

GTCGTTGCCG TACTTGTAAT AATAAGTACC GCAGCCAAAG GCTAATCTTG             100

GAATGCCCGA GGAGGTGGTT GGAATGCTCA TTTCGAATAC AGTCAACAAT             150

CAATTGAGTT TGTATTTATA GCCAATTGGT CATTAATAAT CAGGCTTCCT             200

GCATGGTTTA GAGGTTGGTC TAGACTACAT CCGTGCACCA GAAAAGAGGC             250

GGGCCACGGA GGAAAAGGTG ACAACTCGCA AAGTTGCAAC AACTGCTATG             300

GCTCCAGCAC GGTGCGTGGG GTAAAGACAA TCTCCGGGAA CCGGTCCCGA             350

AACCGAGAAA GAGGGTTTTA AGCCTGTGTC CTCTGCGGAG GTGGTGTAGC             400

ACTTCTTATT GTCCTTTGGG CCGCTCCGGC GGTAGAGCTT CCATGGAACA             450

ACCTTGCACG GACAGGCAAG TCCCCGAGAC GCCTTGTTGG GTGATGTCCA             500

CTTCTGGCTA TACAGAGCTT TATATCACCT TACTGAACGC TAGAGTAGAC             550

CCAATTCCCG GCTCACACCA CCCTTACATG CAGAGCTAAC CAATAAGGTA             600

ATTAATTAAC ACTATATAGC TCGTGGTGAA CACTGGCCCG GAGTAGTCAT             650

ACGTGTAGGT TTTTGGCGTG ATGAAAATCA GGTGGCGCAC GACTTTTCGT             700

AAAGTTCGGG AGGGAGTGCT GCAAACGGCA TATAAGGACC AGTTTTTCTC             750

GCACATTATC AATTGCTCTT TAGTACAAAG ATAATATAGA AACAAT                 796
```

(2) INFORMATION FOR SEQ ID NO: 8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 8:

GAATTAGAGA GG                                                12

(2) INFORMATION FOR SEQ ID NO: 9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 9:

GAATTAGAGC AAGTAG                                            16

(2) INFORMATION FOR SEQ ID NO: 10:

```
    (i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 10:

AAGCTTACCA GTTCTCACAC GG                                           22

(2) INFORMATION FOR SEQ ID NO: 11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 11:

AAGCTTACAA TCAATGAATC GA                                           22

(2) INFORMATION FOR SEQ ID NO: 12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 12:

GAATTCGAAT ATTGTTTCTA TATTATC                                      27

(2) INFORMATION FOR SEQ ID NO: 13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 13:

GTAAAACGAC GGCCAGT                                                 17

(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 14:

GAATTCGTTA TGAGCCATAT TCAA                                         24
```